(12) United States Patent
Bouillot et al.

(10) Patent No.: US 8,207,204 B2
(45) Date of Patent: Jun. 26, 2012

(54) TRIAZOLE DERIVATIVES AS SCD INHIBITORS

(75) Inventors: Anne Marie Jeanne Bouillot, Les Ulis (FR); Alain Laroze, Les Ulis (FR)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/741,629

(22) PCT Filed: Nov. 7, 2008

(86) PCT No.: PCT/EP2008/065105
§ 371 (c)(1),
(2), (4) Date: Aug. 9, 2010

(87) PCT Pub. No.: WO2009/060054
PCT Pub. Date: May 14, 2009

(65) Prior Publication Data
US 2010/0297097 A1    Nov. 25, 2010

(30) Foreign Application Priority Data
Nov. 9, 2007  (GB) .................................. 0722075.9

(51) Int. Cl.
*A61K 31/4192* (2006.01)
*A61K 31/4245* (2006.01)
*C07D 249/06* (2006.01)
*C07D 413/10* (2006.01)

(52) U.S. Cl. .......... 514/359; 514/364; 548/143; 548/255
(58) Field of Classification Search .................. 514/359; 548/255
See application file for complete search history.

(56) References Cited

U.S. PATENT DOCUMENTS

| | | | |
|---|---|---|---|
| 2006/0160794 A1 * | 7/2006 | Amegadzie et al. ....... | 514/227.5 |
| 2010/0022486 A1 | 1/2010 | Bouillot et al. .............. | 514/167 |
| 2010/0041590 A1 | 2/2010 | Bouillot ..................... | 514/9 |
| 2010/0041696 A1 | 2/2010 | Daugan et al. ............... | 514/310 |
| 2010/0048617 A1 | 2/2010 | Daugan ...................... | 514/307 |
| 2010/0120669 A1 | 5/2010 | Bouillot et al. ............. | 514/10 |
| 2010/0297054 A1 | 11/2010 | Bouillot et al. ............ | 424/78.1 |

FOREIGN PATENT DOCUMENTS

| | | |
|---|---|---|
| WO | WO 2006/101521 A | 9/2006 |
| WO | WO 2006/114314 A | 11/2006 |
| WO | WO 2007/009236 A | 1/2007 |
| WO | WO 2009/010560 A1 | 1/2009 |
| WO | WO 2009/016216 A1 | 2/2009 |
| WO | WO 2009/056556 A1 | 5/2009 |
| WO | WO 2009/150196 A1 | 12/2009 |

OTHER PUBLICATIONS

Loaiza, et al (J. Comb. Chem., 2006, vol. 8(2), pp. 252-261).*
Patani, et al., Chem. Rev., 1996, 96, 3147-3176, especially p. 3149.*
Rodionov, et al. *Journal of the American Chemical Society*, 129(42): 12696-12704 (Oct. 24, 2007).

* cited by examiner

*Primary Examiner* — Susannah Chung
(74) *Attorney, Agent, or Firm* — Dara L. Dinner; Theodore Furman

(57) ABSTRACT

The present invention relates to substituted triazole compounds of the formula (I):

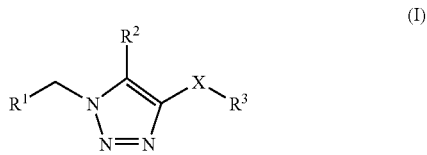

and salts thereof, to pharmaceutical compositions containing them and their use in medicine. In particular, the invention relates to compounds for inhibiting SCD activity, such as diseases related to elevated lipid levels, cardiovascular disease, diabetes, obesity, metabolic syndrome, skin disorders such as acne, diseases or conditions related to cancer and the treatment of symptoms linked to the production of the amyloid plaque-forming Aβ42 peptide such as Alzheimer's disease and the like.

16 Claims, No Drawings

TRIAZOLE DERIVATIVES AS SCD INHIBITORS

This application is a §371 national stage entry of International Application No. PCT/EP2008/065105, filed 7 Nov. 2008, which claims the benefit of priority of GB Application No. 0722075.9, filed 9 Nov. 2007, which are incorporated herein in their entireties.

FIELD OF THE INVENTION

The present invention relates to a novel class of compounds believed to be inhibitors of stearoyl-CoA desaturase (SCD), compositions comprising said compounds, methods of synthesis and uses for such compounds in treating and/or preventing various diseases, including those mediated by SCD enzyme, such as diseases related to elevated lipid levels, cardiovascular disease, diabetes, obesity, metabolic syndrome, skin disorders such as acne, diseases or conditions related to cancer and the treatment of symptoms linked to the production of the amyloid plaque-forming Aβ42 peptide such as Alzheimer's disease and the like.

BACKGROUND OF THE INVENTION

Acyl desaturase enzymes catalyze the formation of double bonds in fatty acids derived from either dietary sources or de novo synthesis in the liver. Mammals synthesise at least three fatty acid desaturases of differing chain length that specifically catalyze the addition of double bonds at the delta-9, delta-6, and delta-5 positions. Stearoyl-CoA desaturases (SCDs) introduce a double bond in the C9-C10 position of saturated fatty acids. The preferred substrates for the enzymes are palmitoyl-CoA (16:0) and stearoyl-CoA (18:0), which are converted to palmitoleoyl-CoA (16:1) and oleoyl-CoA (18:1), respectively. The resulting mono-unsaturated fatty acids may then be employed in the preparation of phospholipids, triglycerides, and cholesteryl esters, in vivo.

A number of mammalian SCD genes have been cloned. For example, two genes have been cloned from rats (SCD1, SCD2) and four SCD genes have been isolated from mice (SCD1, 2, 3 and 4). While the basic biochemical roles of SCD has been known in rats and mice since the 1970's (Jeffcoat, R et al., *Elsevier Science* (1984), Vol 4, pp. 85-112; de Antueno, R J, *Lipids* (1993), Vol. 28, No. 4, pp. 285-290), it has only recently been directly implicated in human diseases processes.

A single SCD gene, SCD1, has been characterized in humans. SCD1 is described in Brownlie et al, WO 01/62954. A second human SCD isoform has been identified, and because it bears little sequence homology to known mouse or rat isoforms it has been named human SCD5 or hSCD5 (WO 02/26944).

Whilst not wishing to be bound by theory, it is thought that inhibition of the activity of SCD in vivo can be used to ameliorate and/or treat one or more diseases such as dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia, metabolic syndrome; other cardiovascular diseases e.g. peripheral vascular disease, reperfusion injury, angioplastic restenosis, hypertension, vascular complications of diabetes, thrombosis; hepatic steatosis, non-alcoholic steatohepatitis (NASH) and other diseases related to accumulation of lipids in the liver.

An SCD-mediated disease or condition also includes a disorder of polyunsaturated fatty acid (PUFA) disorder, or a skin disorder, including but not limited to eczema, acne, psoriasis, skin ageing, keloid scar formation or prevention, diseases related to production or secretions from mucous membranes, such as monounsaturated fatty acids, wax esters, and the like (US2006/0205713A1, WO2007/046868, WO2007/046867). SCD has been shown to play a physiological role in cholesterol homeostasis and the de novo biosynthesis of cholesterol esters, triglycerides and wax esters required for normal skin and eyelid function and therefore may be useful in the treatment of acne and other skin conditions (Makoto et al. J of Nutrition (2001), 131(9), 2260-2268, Harrison et al. J of Investigative Dermatology (2007) 127(6), 1309-1317).

An SCD-mediated disease or condition also includes but is not limited to a disease or condition which is, or is related to cancer, neoplasia, malignancy, metastases, tumours (benign or malignant), carcinogenesis, hepatomas and the like (US2006/0205713A1, WO2007/046868, WO2007/046867). Recently, SCD-1 has been identified as playing a role in human tumor cell survival and therefore has potential as an anticancer target (Morgan-Lappe et al. 2007 Cancer Res. 67(9) 4390-4398).

It has been shown that overexpression of Steroyl-CoA desaturase (SCD) in human cells in culture leads to a specific increase in the production of the amyloid plaque-forming Aβ42 peptide, and conversely, that reductions in SCD activity in human cells in culture leads to a specific decrease in the production of Aβ42. Therefore, SCD inhibitors may also be useful for treating, delaying the onset of symptoms, or slowing the progression of symptoms of mild cognitive impairment (MCI), Alzheimer's Disease (AD), cerebral amyloid angiopathy (CAA) or dementia associated with Down Syndrome (DS) and other neurodegenerative diseases characterized by the formation or accumulation of amyloid plaques comprising Aβ42 (US2007/0087363A1; Myriad Genetics).

WO2005/011657 describes certain piperazine derivatives useful for inhibiting SCD activity.

The present invention provides a compound of formula (I) for inhibiting SCD activity:

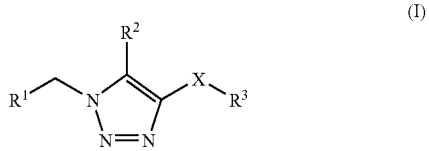

(I)

wherein:
X represents —CONH—, —NHCO— or —CH$_2$NH—;
R$^1$ represents:
—C$_{6-10}$aryl (such as phenyl) optionally substituted by one, two or three groups independently selected from:

—C$_{1-3}$alkyl (such as —CH$_3$), —C$_{1-6}$alkoxy (such as —OCH$_3$), —C$_{1-6}$haloalkyl (such as —CF$_3$), —OC$_{1-6}$haloalkyl (such as —OCF$_3$), —OC$_{3-6}$cycloalkyl or halogen (such as chloro, bromo or fluoro);

R$^2$ represents hydrogen, —C$_{1-6}$alkyl (such as —CH$_3$) or —C$_{1-3}$alkylOC$_{1-3}$alkyl (such as —CH$_2$OCH$_3$);

R$^3$ represents:

—C$_{5-9}$heteroaryl optionally substituted by one, two or three groups independently selected from: —C$_{1-3}$alkyl (such as —CH$_3$), —C$_{1-6}$alkoxy (such as —OCH$_3$), —CO$_2$R$^4$, —C(=O)NR$^5$R$^6$, —C(=O)NHC$_{1-3}$alkylNR$^7$R$^8$, —C(=O)NHC$_{1-3}$alkylOC$_{1-3}$alkyl, —C(=O)NHC$_{1-3}$alkylOH, —C(=O)R$^9$, —C$_{1-6}$alkylOH (such as —CH$_2$OH or —C$_2$H$_4$OH), —C=O, —CHO, —C$_{1-3}$alkylCO$_2$C$_{1-3}$alkyl, —C$_{1-3}$alkylOC$_{1-3}$alkyl, —C$_{1-6}$haloalkyl (such as —CF$_3$), —OC$_{1-6}$haloalkyl (such as —OCF$_3$), —OC$_{3-6}$cycloalkyl, —C$_{3-6}$cycloalkyl, or halogen (such as chloro, bromo or fluoro);

R$^4$ represents —H or —C$_{1-3}$alkyl (such as —CH$_3$ or —C$_2$H$_5$);

R$^5$ represents —H or —C$_{1-3}$alkyl (such as —CH$_3$);
R$^6$ represents —H or —C$_{1-6}$alkyl (such as —CH$_3$);
R$^7$ represents —H or —C$_{1-3}$alkyl (such as —CH$_3$);
R$^8$ represents —H or —C$_{1-3}$alkyl (such as —CH$_3$); and
R$^9$ represents —C$_6$heterocycle (such as morpholine or piperazine) which is optionally substituted by a group independently selected from: —C$_{1-6}$alkyl (such as —CH$_3$);

or a pharmaceutically acceptable salt thereof,
with the proviso that the compound of formula (I) is not
N-1,3-benzodioxol-5-yl-1-[(4-fluorophenyl)methyl]-1H-1,2,3-triazole-4-carboxamide

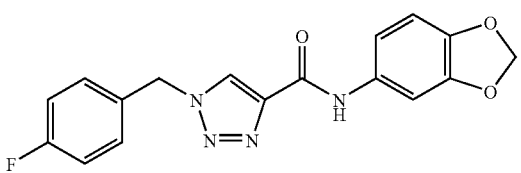

or N-(6-acetyl-1,3-benzodioxol-5-yl)-1-[(4-methylphenyl)methyl]-1H-1,2,3-triazole-4-carboxamide

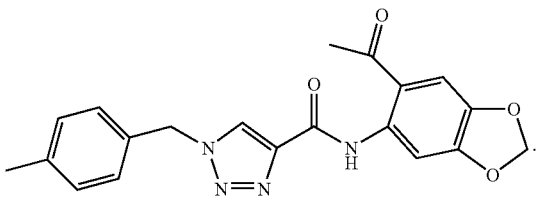

The said compounds have been found to inhibit SCD activity and may therefore be useful in the treatment of SCD-mediated diseases such as diseases or conditions caused by or associated with an abnormal plasma lipid profile including dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia and metabolic syndrome; other cardiovascular diseases e.g. peripheral vascular disease, reperfusion injury, angioplastic restenosis, hypertension, vascular complications of diabetes, thrombosis, hepatic steatosis, non-alcoholic steatoheptatis (NASH) and other diseases related to accumulation of lipids in the liver; skin disorders e.g. eczema, acne, psoriasis, skin ageing, keloid scar formation or prevention, and diseases related to production or secretions from mucous membranes; cancer, neoplasia, malignancy, metastases, tumours (benign or malignant), carcinogenesis, hepatomas and the like; mild cognitive impairment (MCI), Alzheimer's Disease (AD), cerebral amyloid angiopathy (CAA) or dementia associated with Down Syndrome (DS) and other neurodegenerative diseases characterized by the formation or accumulation of amyloid plaques comprising Aβ42.

In one aspect of the invention, X represents —CONH—. In another aspect of the invention, X represents —NHCO—. In another aspect of the invention, X represents —CH$_2$NH—.

In one aspect of the invention, R$^1$ represents phenyl optionally substituted by one, two or three groups independently selected from: —C$_{1-3}$alkyl (such as —CH$_3$), —C$_{1-6}$alkoxy (such as —OCH$_3$), —C$_{1-6}$haloalkyl (such as —CF$_3$), —OC$_{1-6}$haloalkyl (such as —OCF$_3$), —OC$_{3-6}$cycloalkyl or halogen (such as chloro, bromo or fluoro).

In another aspect of the invention, R$^1$ represents phenyl optionally substituted by one or two groups independently selected from: —C$_{1-3}$alkyl (such as —CH$_3$), —C$_{1-6}$alkoxy (such as —OCH$_3$), —C$_{1-6}$haloalkyl (such as —CF$_3$), —OC$_{1-6}$haloalkyl (such as —OCF$_3$), —OC$_{3-6}$cycloalkyl or halogen (such as chloro, bromo or fluoro).

In another aspect of the invention, R$^1$ represents phenyl optionally substituted by one, two or three groups independently selected from: —C$_{1-3}$alkyl (such as —CH$_3$), —C$_{1-3}$alkoxy (such as —OCH$_3$), —C$_{1-3}$haloalkyl (such as —CF$_3$), —OC$_{1-3}$haloalkyl (such as —OCF$_3$), —OC$_{3-6}$cycloalkyl or halogen (such as chloro, bromo or fluoro).

In another aspect of the invention, R$^1$ represents phenyl optionally substituted by one or two groups independently selected from: —C$_{1-3}$alkyl (such as —CH$_3$), —C$_{1-3}$alkoxy (such as —OCH$_3$), —C$_{1-3}$haloalkyl (such as —CF$_3$), —OC$_{1-3}$haloalkyl (such as —OCF$_3$), —OC$_{3-6}$cycloalkyl or halogen (such as chloro, bromo or fluoro).

In another aspect of the invention, R$^1$ represents phenyl optionally substituted by one, two or three groups independently selected from: —CH$_3$, —OCH$_3$, —CF$_3$, —OCF$_3$ or halogen (such as chloro, bromo or fluoro).

In another aspect of the invention, R$^1$ represents phenyl optionally substituted by one or two groups independently selected from: —CH$_3$, —OCH$_3$, —CF$_3$, —OCF$_3$ or halogen (such as chloro, bromo or fluoro).

In another aspect of the invention, R$^1$ represents phenyl substituted by two groups independently selected from halogen (such as chloro, bromo or fluoro).

In another aspect of the invention, R$^1$ represents phenyl substituted by two chloro groups.

In another aspect of the invention, R$^1$ is phenyl substituted in the meta position, that is in the 3 position, and the para position, that is in the 4 position, by halogen e.g chloro i.e.

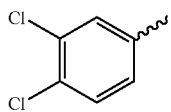

In another aspect of the invention, $R^1$ is phenyl substituted in the meta position, that is in the 3 position and 5 position, by halogen e.g chloro i.e

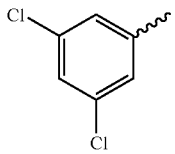

In another aspect of the invention, $R^1$ represents phenyl.

In one aspect of the invention, $R^2$ represents hydrogen. In another aspect of the invention, $R^2$ represents —$C_{1-6}$alkyl. In another aspect of the invention, $R^2$ represents —$C_{1-3}$alkyl. In another aspect of the invention, $R^2$ represents —$CH_3$ (methyl). In another aspect of the invention, $R^2$ represents —$C_{1-3}$alkyl$OC_{1-3}$alkyl. In another aspect of the invention, $R^2$ represents —$CH_2OCH_3$. In another aspect of the invention, $R^2$ represents hydrogen or —$C_{1-3}$alkyl.

In one aspect of the invention, $R^3$ represents a —$C_{5-9}$heteroaryl wherein the optional substituent is on a carbon atom.

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one, two or three groups independently selected from: —$C_{1-3}$alkyl (such as —$CH_3$), —$C_{1-6}$alkoxy (such as —$OCH_3$), —$CO_2R^4$, —$C(=O)NR^5R^6$, —$C(=O)NHC_{1-3}$alkyl$NR^7R^8$, —$C(=O)NH C_{1-3}$alkyl$OC_{1-3}$alkyl, —$C(=O)NHC_{1-3}$alkylOH, —$C(=O)R^9$, —$C_{1-6}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-6}$haloalkyl (such as —$CF_3$), —$OC_{1-6}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one or two groups independently selected from: —$C_{1-3}$alkyl (such as —$CH_3$), —$C_{1-6}$alkoxy (such as —$OCH_3$), —$CO_2R^4$, —$C(=O)NR^5R^6$, —$C(=O)NHC_{1-3}$alkyl$NR^7R^8$, —$C(=O)NHC_{1-3}$alkyl$OC_{1-3}$alkyl, —$C(=O)NHC_{1-3}$alkylOH, —$C(=O)R^9$, —$C_{1-6}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-6}$haloalkyl (such as —$CF_3$), —$OC_{1-6}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one, two or three groups independently selected from: —$C_{1-3}$alkyl (such as —$CH_3$), —$C_{1-3}$alkoxy (such as —$OCH_3$), —$CO_2R^4$, —$C(=O)NR^5R^6$, —$C(=O)NHC_{1-3}$alkyl$NR^7R^8$, —$C(=O)NH C_{1-3}$alkyl$OC_{1-3}$alkyl, —$C(=O)NHC_{1-3}$alkylOH, —$C(=O)R^9$, —$C_{1-3}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl or —$C_{1-3}$haloalkyl (such as —$CF_3$).

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one or two groups independently selected from: —$C_{1-3}$alkyl (such as —$CH_3$), —$C_{1-3}$alkoxy (such as —$OCH_3$), —$CO_2R^4$, —$C(=O)NR^5R^6$, —$C(=O)NHC_{1-3}$alkyl$NR^7R^8$, —$C(=O)NHC_{1-3}$alkyl$OC_{1-3}$alkyl, —$C(=O)NHC_{1-3}$alkylOH, —$C(=O)R^9$, —$C_{1-3}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl or —$C_{1-3}$haloalkyl (such as —$CF_3$).

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one, two or three groups independently selected from: —$C_{1-3}$alkyl (such as —$CH_3$), —$CO_2R^4$, —$C(=O)NR^5R^6$, —$C(=O)NH C_{1-3}$alkyl$N(CH_3)_2$, —$C(=O)NHC_{1-3}$alkyl$OC_{1-3}$alkyl, —$C(=O)NHC_{1-3}$alkylOH, —$C(=O)R^9$, —$C_{1-3}$alkylOH (such as —$CH_2OH$ or —$C_2H_4OH$), —CHO, —$C_{1-3}$alkyl$CO_2 C_{1-3}$alkyl, —$C_{1-3}$alkyl$OC_{1-3}$alkyl or —$C_{1-3}$haloalkyl (such as —$CF_3$).

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one or two groups independently selected from: —$C_{1-3}$alkyl (such as —$CH_3$), —$CO_2R^4$, —$C(=O)NR^5R^6$, —$C(=O)NHC_{1-3}$alkyl$N(CH_3)_2$, —$C(=O)NHC_{1-3}$alkyl$OC_{1-3}$alkyl, —$C(=O)NHC_{1-3}$alkylOH, —$C(=O)R^9$, —$C_{1-3}$alkylOH (such as —$CH_2OH$ or —$C_2H_4OH$), —CHO, —$C_{1-3}$alkyl$CO_2C_{1-3}$alkyl, —$C_{1-3}$alkyl$OC_{1-3}$alkyl or —$C_{1-3}$haloalkyl (such as —$CF_3$).

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one, two or three groups independently selected from: —$CH_3$, —$CO_2H$, —$CO_2CH_3$, —$CO_2C_2H_5$, —$C(=O)NH_2$, —$C(=O)NHCH_3$, —$C(=O)NHC_2H_5$, —$C(=O)NHCH(CH_3)_2$, —$C(=O)NHC_2H_4CH(CH_3)_2$, —$C(=O)N(CH_3)_2$—$C(=O)NHC_2H_4N(CH_3)_2$, —$C(=O)NHC_2H_4OH$, —$C(=O)NHC_2H_4OCH_3$, —$C(=O)R^9$, —$CH_2OH$, —$C_2H_4OH$, —CHO, —$CH_2CO_2CH_3$, —$CH_2CO_2C_2H_5$—$CH_2OCH_3$, —$CH_2CONHCH_3$ or —$CF_3$.

In another aspect of the invention, $R^3$ represents —$C_5$heteroaryl containing 5 ring-atoms 1, 2, 3 or 4 of which are hetero-atoms independently selected from nitrogen, oxygen or sulphur and the remaining ring-atoms are carbon, optionally substituted by one or two groups independently selected from: —$CH_3$, —$CO_2H$, —$CO_2CH_3$, —$CO_2C_2H_5$, —C(=O)$NH_2$, —C(=O)$NHCH_3$, —C(=O)$NHC_2H_5$, —C(=O)$NHCH(CH_3)_2$, —C(=O)$NHC_2H_4CH(CH_3)_2$, —C(=O)N($CH_3$)$_2$—C(=O)$NHC_2H_4N(CH_3)_2$, —C(=O)$NHC_2H_4OH$, —C(=O)$NHC_2H_4OCH_3$, —C(=O)$R^9$, —$CH_2OH$, —$C_2H_4OH$, —CHO, —$CH_2CO_2CH_3$, —$CH_2CO_2C_2H_5$—$CH_2OCH_3$, —$CH_2CONHCH_3$ or —$CF_3$.

In another aspect of the invention, $R^3$ represents thiazole, thiadiazole, oxadiazole or oxazole, optionally substituted by one, two or three groups independently selected from: —$CH_3$, —$CO_2H$, —$CO_2CH_3$, —$CO_2C_2H_5$, —C(=O)$NH_2$, —C(=O)$NHCH_3$, —C(=O)$NHC_2H_5$, —C(=O)NHCH($CH_3$)$_2$, —C(=O)$NHC_2H_4CH(CH_3)_2$, —C(=O)N($CH_3$)$_2$—C(=O)$NHC_2H_4N(CH_3)_2$, —C(=O)$NHC_2H_4OH$, —C(=O)$NHC_2H_4OCH_3$, —C(=O)$R^9$, —$CH_2OH$, —$C_2H_4OH$, —CHO, —$CH_2CO_2CH_3$, —$CH_2CO_2C_2H_5$—$CH_2OCH_3$, —$CH_2CONHCH_3$ or —$CF_3$.

In another aspect of the invention, $R^3$ represents thiazole, thiadiazole, oxadiazole or oxazole, optionally substituted by one or two groups independently selected from: —$CH_3$, —$CO_2H$, —$CO_2CH_3$, —$CO_2C_2H_5$, —C(=O)$NH_2$, —C(=O)$NHCH_3$, —C(=O)$NHC_2H_5$, —C(=O)NHCH($CH_3$)$_2$, —C(=O)$NHC_2H_4CH(CH_3)_2$, —C(=O)N($CH_3$)$_2$—C(=O)$NHC_2H_4N(CH_3)_2$, —C(=O)$NHC_2H_4OH$, —C(=O)$NHC_2H_4OCH_3$, —C(=O)$R^9$, —$CH_2OH$, —$C_2H_4OH$, —CHO, —$CH_2CO_2CH_3$, —$CH_2CO_2C_2H_5$—$CH_2OCH_3$, —$CH_2CONHCH_3$ or —$CF_3$.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$C_{1-3}$alkyl (such as —$CH_3$), —$C_{1-6}$alkoxy (such as —$OCH_3$), —$CO_2R^4$, —C(=O)$NR^5R^6$, —C(=O)$NHC_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-6}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-6}$haloalkyl (such as —$CF_3$), —$OC_{1-6}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one or two groups independently selected from: —$C_{1-3}$alkyl (such as —$CH_3$), —$C_{1-6}$alkoxy (such as —$OCH_3$), —$CO_2R^4$, —C(=O)$NR^5R^6$, —C(=O)NH$C_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-6}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-6}$haloalkyl (such as —$CF_3$), —$OC_{1-6}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$C_{1-3}$alkyl (such as —$CH_3$), —$C_{1-3}$alkoxy (such as —$OCH_3$), —$CO_2R^4$, —C(=O)$NR^5R^6$, —C(=O)NH$C_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-3}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-3}$haloalkyl (such as —$CF_3$), —$OC_{1-3}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one or two groups independently selected from: —$C_{1-3}$alkyl (such as —$CH_3$), —$C_{1-3}$alkoxy (such as —$OCH_3$), —$CO_2R^4$, —C(=O)$NR^5R^6$, —C(=O)NH$C_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-3}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-3}$haloalkyl (such as —$CF_3$), —$OC_{1-3}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$C_{1-6}$alkoxy (such as —$OCH_3$), —$CO_2R^4$ or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one or two groups independently selected from: —$C_{1-6}$alkoxy (such as —$OCH_3$), —$CO_2R^4$ or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$C_{1-3}$alkoxy (such as —$OCH_3$), —$CO_2R^4$ or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one or two groups independently selected from: —$C_{1-3}$alkoxy (such as —$OCH_3$), —$CO_2R^4$ or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$OCH_3$, —$CO_2C_{1-3}$alkyl or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one or two groups independently selected from: —$OCH_3$, —$CO_2C_{1-3}$alkyl or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$OCH_3$, —$CO_2C_2H_5$ or —C=O.

In another aspect of the invention, $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one or two groups independently selected from: —$OCH_3$, —$CO_2C_2H_5$ or —C=O.

In another aspect of the invention, $R^3$ represents benzothiazole or thiazolo-pyrimidin, optionally substituted by one, two or three groups independently selected from: —$OCH_3$, —$CO_2C_2H_5$ or —C=O.

In another aspect of the invention, $R^3$ represents benzothiazole or thiazolo-pyrimidin, optionally substituted by one or two groups independently selected from: —$OCH_3$, —$CO_2C_2H_5$ or —C=O.

In another aspect of the invention, $R^3$ represents —$C_6$heteroaryl optionally substituted by one, two or three groups independently selected from: —$C_{1-3}$alkyl (such as —$CH_3$), —$C_{1-6}$alkoxy (such as —$OCH_3$), —$CO_2R^4$, —C(=O)$NR^5R^6$, —C(=O)$NHC_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-6}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-6}$haloalkyl (such as —$CF_3$), —$OC_{1-6}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_6$heteroaryl optionally substituted by one or two groups independently selected from: —$C_{1-3}$alkyl (such as —$CH_3$), —$C_{1-6}$alkoxy (such as —$OCH_3$), —$CO_2R^4$, —C(=O)$NR^5R^6$, —C(=O)$NHC_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-6}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-6}$haloalkyl (such as —$CF_3$), —$OC_{1-6}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents —$C_6$heteroaryl optionally substituted by one, two or three groups independently selected from: —$C_{1-3}$alkyl (such as —$CH_3$), —$C_{1-3}$alkoxy (such as —$OCH_3$), —$CO_2R^4$, —C(=O)$NR^5R^6$, —C(=O)$NHC_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-3}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-3}$haloalkyl (such as —$CF_3$), —$OC_{1-3}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents pyridine optionally substituted by one or two groups independently selected from: —$C_{1-3}$alkyl (such as —$CH_3$), —$C_{1-3}$alkoxy (such as —$OCH_3$), —$CO_2R^4$, —C(=O)$NR^5R^6$, —C(=O)$NHC_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-3}$alkylOH (such as —$CH_2OH$ or —$C_2H_4OH$), —C=O, —CHO, —$C_{1-3}$alkyl$CO_2C_{1-3}$alkyl, —$C_{1-3}$alkyl$OC_{1-3}$alkyl, —$C_{1-3}$haloalkyl (such as —$CF_3$), —$OC_{1-3}$haloalkyl (such as —$OCF_3$), —$OC_{3-6}$cycloalkyl, —$C_{3-6}$cycloalkyl or halogen (such as chloro, bromo or fluoro).

In another aspect of the invention, $R^3$ represents pyridine optionally substituted by one, two or three groups independently selected from: —$CO_2R^4$, —$C_{1-6}$alkylOH (such as —$CH_2OH$ or —$C_2H_4OH$) or —C(=O)$NR^5R^6$.

In another aspect of the invention, $R^3$ represents pyridine optionally substituted by one or two groups independently selected from: —$CO_2R^4$, —$C_{1-6}$alkylOH (such as —$CH_2OH$ or —$C_2H_4OH$) or —C(=O)$NR^5R^6$.

In another aspect of the invention, $R^3$ represents pyridine optionally substituted by one or two groups independently selected from: —$CO_2R^4$, —$C_{1-3}$alkylOH (such as —$CH_2OH$ or —$C_2H_4OH$) or —C(=O)$NR^5R^6$.

In another aspect of the invention, $R^3$ represents pyridine optionally substituted by a group independently selected from: —$CO_2R^4$, —$C_{1-3}$alkylOH (such as —$CH_2OH$ or —$C_2H_4OH$) or —C(=O)$NR^5R^6$.

In another aspect of the invention, $R^3$ represents pyridine optionally substituted by a group independently selected from: —$CO_2CH_3$, —$CH_2OH$ or —$CONHCH_3$.

In one aspect of the invention, $R^4$ represents hydrogen. In another aspect of the invention, $R^4$ represents —$C_{1-3}$alkyl. In another aspect of the invention, $R^4$ represents —$C_2H_5$ (ethyl). In another aspect of the invention, $R^4$ represents —$CH_3$ (methyl).

In one aspect of the invention, $R^5$ represents hydrogen. In another aspect of the invention $R^5$ represents —$C_{1-3}$alkyl. In another aspect of the invention $R^5$ represents —$CH_3$ (methyl).

In one aspect of the invention, $R^6$ represents hydrogen. In another aspect of the invention, $R^6$ represents —$C_{1-6}$alkyl. In another aspect of the invention $R^6$ represents —$C_{1-3}$alkyl. In another aspect of the invention, $R^6$ represents —$CH_3$ (methyl). In another aspect of the invention, $R^6$ represents —CH$(CH_3)_2$ (isopropyl). In another aspect of the invention, $R^6$ represents —$C_2H_5$ (ethyl). In another aspect of the invention, $R^6$ represents —$C_3H_7$ (propyl).

In one aspect of the invention, $R^7$ represents hydrogen. In another aspect of the invention, $R^7$ represent —$C_{1-3}$alkyl. In another aspect of the invention, $R^7$ represents —$CH_3$ (methyl).

In one aspect of the invention, $R^8$ represents hydrogen. In another aspect of the invention, $R^8$ represent —$C_{1-3}$alkyl. In another aspect of the invention, $R^8$ represents —$CH_3$ (methyl).

In one aspect of the invention, $R^9$ represents morpholine or piperazine optionally substituted by —$C_{1-6}$alkyl (such as —$CH_3$). In another aspect of the invention, $R^9$ represents morpholine or piperazine optionally substituted by —$C_{1-3}$alkyl (such as —$CH_3$). In another aspect of the invention, $R^9$ represents morpholine or piperazine substituted by —$CH_3$ (methyl).

Each of the aspects of the invention are independent unless stated otherwise. Nevertheless the skilled person will understand that all the permutations of the aspects of described are within the scope of the invention. Thus it is to be understood that the present invention covers all combinations of suitable, convenient and exemplified groups described herein. For example, in one aspect the invention provides a compound of formula (I) wherein X represents —CONH— and $R^2$ represents —$CH_3$.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The invention also extends to conformational isomers of compounds of formula (I) and any geometric (cis and/or trans) isomers of said compounds. Likewise, it is understood that compounds of formula (I) may exist in tautomeric forms other than that shown in the formula and these are also included within the scope of the present invention.

It will be appreciated that racemic compounds of formula (I) may be optionally resolved into their individual enantiomers. Such resolutions may conveniently be accomplished by standard methods known in the art. For example, a racemic compound of formula (I) may be resolved by chiral preparative HPLC.

It will also be appreciated that compounds of the invention which exist as polymorphs, and mixtures thereof, are within the scope of the present invention.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl. However, when a moiety is defined such that alkyl bears a substituent it will be clear to the skilled person from the context that alkyl may include alkylene, for example methylene (—$CH_2$—), ethylene (—$CH_2CH_2$—) and propylene (—$CH_2CH_2CH_2$—).

As used herein, the term "alkylOH" refers to straight or branched hydrocarbon chains containing the specified number of carbon atoms and a hydroxyl group. For example, —$C_{1-6}$alkylOH means a straight or branched alkyl containing at least 1, and at most 6, carbon atoms and OH. In one aspect of the invention, the alkyl chain in —$C_{1-6}$alkylOH is a straight hydrocarbon chain containing the specified number of carbon atoms and a hydroxyl group.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. The point of attachment may be on the oxygen or carbon atom.

As used herein, the term "halogen" or "halo" refers to a fluorine (fluoro), chlorine (chloro), bromine (bromo) or iodine (iodo) atom.

As used herein, the term "haloalkyl" refers to an alkyl group having one or more carbon atoms and wherein at least one hydrogen atom is replaced with a halogen atom, for example a trifluoromethyl group and the like.

As used herein, the term "cycloalkyl" refers to a saturated cyclic group containing 3 to 6 carbon ring-atoms. Examples include cyclopropyl, cyclopentyl and cyclohexyl.

As used herein, the term "$C_{5-9}$heteroaryl" refers to an aromatic cyclic group containing 5 to 9 ring-atoms 1, 2, 3 or 4 of which are hetero-atoms independently selected from nitrogen, oxygen and sulphur and the remaining ring-atoms are carbon, e.g. isoxazole, oxazole, thiazolopyrimidine, imidazole, thiazole, benzothiazole, thiadiazole, oxadiazole or pyridine and more specifically thiazole, benzothiazole, thiadiazole, oxazole, pyridine and thiazolopyrimidine. This definition includes both monocyclic and bicyclic ring systems and bicyclic structures at least a portion of which is aromatic and the other part is saturated, partially or fully unsaturated.

As used herein, the term '—$C_{6-10}$aryl' means an aromatic carbocyclic moiety containing 6 to 10 ring-atoms. The definition includes both monocyclic and bicyclic ring systems and bicyclic structures at least a portion of which is aromatic and the other part is saturated, partially or fully unsaturated. Examples of aromatic, aryl groups include phenyl, naphthyl, anthryl, phenanthryl, indanyl, indenyl, azulenyl, azulanyl, fluorenyl, more specifically phenyl and naphthyl, and more specifically phenyl.

As used herein, the term "$C_6$heterocyclyl" refers to a cyclic group containing 6 ring-atoms 1, 2 or 3 of which are hetero-atoms independently selected from nitrogen, oxygen and sulphur and the remaining ring-atoms are carbon, and, wherein said cyclic group is saturated, partially or fully unsaturated but, which is not aromatic e.g 1,4-dioxane, morpholine, 1,4-dithiane, piperazine, piperidine, tetrahydropyran, dihydropyran, 1,3-dioxane, 1,3-dithiane, oxathiane or thiomorpholine and more specifically morpholine and piperazine. This definition includes bicyclic structures provided the moiety is non-aromatic.

Examples of heterocyclyl and heteroaryl groups include: furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, homopiperazinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl, benzimidazolyl, benzoxazolyl, imidazopyridinyl, benzoxazinyl, benzothiazinyl, benzothiophenyl oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl.

As used herein, the term "substituted" refers to substitution with the named substituent or substituents, multiple degrees of substitution being allowed unless otherwise stated.

For the avoidance of doubt, the term "independently" means that where more than one substituent is selected from a number of possible substituents, those substituents may be the same or different.

As used herein, the term "pharmaceutically acceptable" means a compound which is suitable for pharmaceutical use.

Salts of compounds of formula (I) which are suitable for use in medicine are those wherein the counterion is pharmaceutically acceptable. However, salts having non-pharmaceutically acceptable counterions are within the scope of the present invention, for example, for use as intermediates in the preparation of other compounds of formula (I) and their pharmaceutically acceptable salts.

Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, malic, mandelic, acetic, fumaric, glutamic, lactic, citric, tartaric, benzoic, benzenesulfonic, p-toluenesulfonic, methanesulfonic, ethanesulfonic or naphthalenesulfonic acid. Other non-pharmaceutically acceptable salts e.g. oxalates, may be used, for example in the isolation of compounds of formula (I) and are included within the scope of this invention. Reference is made to Berge et al. J. Pharm. Sci., 1977, 66, 1-19.

Certain of the compounds of formula (I) may form acid addition salts with one or more equivalents of the acid. The present invention includes within its scope all possible stoichiometric and non-stoichiometric forms thereof.

Solvates of the compounds of formula (I) and solvates of the salts of the compounds of formula (I) are included within the scope of the present invention.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include, but are not limited to, water, methanol, ethanol and acetic acid. In one aspect of the invention, the solvent used is a pharmaceutically acceptable solvent. In another aspect of the invention, the solvent used is water and the solvate may also be referred to as a hydrate.

Solvates of compounds of formula (I) which are suitable for use in medicine are those wherein the solvent is pharmaceutically acceptable. However, solvates having non-pharmaceutically acceptable solvents are within the scope of the present invention, for example, for use as intermediates in the preparation of other compounds of formula (I) and their pharmaceutically acceptable salts.

Prodrugs of the compounds of formula (I) are included within the scope of the present invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987 and in D. Fleishner, S. Ramon and H. Barba "Improved oral drug delivery: solubility limitations overcome by the use of prodrugs", Advanced Drug Delivery Reviews (1996) 19(2) 115-130. Prodrugs are any covalently bonded carriers that release a compound of structure (I) in vivo when such prodrug is administered to a patient. Prodrugs are generally prepared by modifying functional groups in a way such that the modification is cleaved in vivo yielding the parent compound. Prodrugs may include, for example, compounds of this invention wherein hydroxyl or amine groups are bonded to any group that, when administered to a patient, cleaves to form the hydroxy or amine groups. Thus, representative examples of prodrugs include (but are not limited to) phosphonate, carbamate, acetate, formate and benzoate derivatives of hydroxy and amine functional groups of the compounds of formula (I).

Phosphonates, acetates, benzoates and carbamates may be active in their own right and/or be hydrolysable under in vivo conditions in the human body. Suitable pharmaceutically acceptable in vivo hydrolysable ester groups include those which break down readily in the human body to leave the parent acid or its salt. A phosphonate is formed by reaction with phosphorous (phosphonic) acid, by methods well known in the art. For example, phosphonates may be derivatives such as RP(O)(OR)$_2$ and the like. A acetate is an ester of acetic acid. A benzoate is an ester of benzenecarboxylic acid. A carbamate is an ester of carbamic acid.

In one aspect of the invention there is provided a compound, or a pharmaceutically acceptable salt thereof, wherein the compound is selected from the group consisting of:

1-[(3,4-Dichlorophenyl)methyl]-5-methyl-N-[6-(methyloxy)-1,3-benzothiazol-2-yl]-1H-1,2,3-triazole-4-carboxamide, Ethyl 2-[({1-[(3,4-dichlorophenyl)methyl]-5-methyl-1H-1,2,3-triazol-4-yl}carbonyl)amino]-4-methyl-1,3-thiazole-5-carboxylate, Ethyl 5-[({1-[(3,4-dichlorophenyl)methyl]-5-methyl-1H-1,2,3-triazol-4-yl}carbonyl)amino]-1,3,4-thiadiazole-2-carboxylate, Methyl 2-[({1-[(3,4-dichlorophenyl)methyl]-5-methyl-1H-1,2,3-triazol-4-yl}carbonyl)amino]-1,3-thiazole-5-carboxylate, 1-[(3,4-Dichlorophenyl)methyl]-N-(5-formyl-1,3-thiazol-2-yl)-5-methyl-1H-1,2,3-triazole-4-carboxamide, 1-[(3,4-Dichlorophenyl)methyl]-5-methyl-N-(5-methyl-1,3,4-oxadiazol-2-yl)-1H-1,2,3-triazole-4-carboxamide, 1-[(3,4-Dichlorophenyl)methyl]-5-methyl-N-{5-[(methyloxy)methyl]-1,3,4-thiadiazol-2-yl}-1H-1,2,3-triazole-4-carboxamide, Methyl {2-[({1-[(3,4-dichlorophenyl)methyl]-5-methyl-1H-1,2,3-triazol-4-yl}carbonyl)amino]-1,3-thiazol-4-yl}acetate, Ethyl 2-[({1-[(3,4-dichlorophenyl)methyl]-5-methyl-1H-1,2,3-triazol-4-yl}carbonyl)amino]-4-(trifluoromethyl)-1,3-thiazole-5-carboxylate, 1-[(3,4-Dichlorophenyl)methyl]-N-(4,5-dimethyl-1,3-thiazol-2-yl)-5-methyl-1H-1,2,3-triazole-4-carboxamide, Ethyl 2-[({1-[(3,4-dichlorophenyl)methyl]-5-methyl-1H-1,2,3-triazol-4-yl}carbonyl)amino]-1,3-benzothiazole-6-carboxylate, Ethyl {2-[({1-[(3,4-dichlorophenyl)methyl]-5-methyl-1H-1,2,3-triazol-4-yl}carbonyl)amino]-5-methyl-1,3-thiazol-4-yl}acetate, 1-[(3,4-Dichlorophenyl)methyl]-N-(5,7-dioxo-4,5,6,7-tetrahydro[1,3]thiazolo[4,5-d]pyrimidin-2-yl)-5-methyl-1H-1,2,3-triazole-4-carboxamide, Methyl 6-[({1-[(3,4-dichlorophenyl)methyl]-5-methyl-1H-1,2,3-triazol-4-yl}carbonyl)amino]-3-pyridinecarboxylate, Methyl 2-[({1-[(3,4-dichlorophenyl)methyl]-5-methyl-1H-1,2,3-triazol-4-yl}carbonyl)amino]-4-pyridinecarboxylate, 2-[({1-[(3,4-Dichlorophenyl)methyl]-5-methyl-1H-1,2,3-triazol-4-yl}carbonyl)amino]-4-methyl-1,3-thiazole-5-carboxylic acid, 2-[({1-[(3,4-dichlorophenyl)methyl]-5-methyl-1H-1,2,3-triazol-4-yl}carbonyl)amino]-1,3-oxazole-5-carboxylic acid, 1-[(3,4-Dichlorophenyl)methyl]-5-methyl-N-{4-methyl-5-[(methylamino)carbonyl]-1,3-thiazol-2-yl}-1H-1,2,3-triazole-4-carboxamide, 1-[(3,4-Dichlorophenyl)methyl]-5-methyl-N-(4-methyl-5-{[(3-methylbutyl)amino]carbonyl}-1,3-thiazol-2-yl)-1H-1,2,3-triazole-4-carboxamide, 1-[(3,4-Dichlorophenyl)methyl]-5-methyl-N-(4-methyl-5-{[(1-methylethyl)amino]carbonyl}-1,3-thiazol-2-yl)-1H-1,2,3-triazole-4-carboxamide, 1-[(3,4-Dichlorophenyl)methyl]-N-{5-[(ethylamino)carbonyl]-4-methyl-1,3-thiazol-2-yl}-5-methyl-1H-1,2,3-triazole-4-carboxamide, 1-[(3,4-Dichlorophenyl)methyl]-N-[5-({[2-(dimethylamino)ethyl]amino}carbonyl)-4-methyl-1,3-thiazol-2-yl]-5-methyl-1H-1,2,3-triazole-4-carboxamide, 1-[(3,4-Dichlorophenyl)methyl]-5-methyl-N-(5-{[(3-methylbutyl)amino]carbonyl}-1,3-thiazol-2-yl)-1H-1,2,3-triazole-4-carboxamide, 1-[(3,4-Dichlorophenyl)methyl]-5-methyl-N-[4-methyl-5-(4-morpholinylcarbonyl)-1,3-thiazol-2-yl]-1H-1,2,3-triazole-4-carboxamide, 1-[(3,4-Dichlorophenyl)methyl]-5-methyl-N-{4-methyl-5-[(4-methyl-1-piperazinyl)carbonyl]-1,3-thiazol-2-yl}-1H-1,2,3-triazole-4-carboxamide, 1-[(3,4-Dichlorophenyl)methyl]-5-methyl-N-[4-methyl-5-({[2-(methyloxy)ethyl]amino}carbonyl)-1,3-thiazol-2-yl]-1H-1,2,3-triazole-4-carboxamide, 1-[(3,4-Dichlorophenyl)methyl]-N-(5-{[(2-hydroxyethyl)amino]carbonyl}-4-methyl-1,3-thiazol-2-yl)-5-methyl-1H-1,2,3-triazole-4-carboxamide, 1-[(3,4-Dichlorophenyl)methyl]-N-{5-[(dimethylamino)carbonyl]-4-methyl-1,3-thiazol-2-yl}-5-methyl-1H-1,2,3-triazole-4-carboxamide, 1-[(3,4-Dichlorophenyl)methyl]-5-methyl-N-{5-[(methylamino)carbonyl]-1,3-thiazol-2-yl}-1H-1,2,3-triazole-4-carboxamide, 1-[(3,4-Dichlorophenyl)methyl]-N-{5-[(dimethylamino)carbonyl]-1,3-thiazol-2-yl}-5-methyl-1H-1,2,3-triazole-4-carboxamide, 1-[(3,4-Dichlorophenyl)methyl]-N-(5-{[(2-hydroxyethyl)amino]carbonyl}-1,3-thiazol-2-yl)-5-methyl-1H-1,2,3-triazole-4-carboxamide, 2-[({1-[(3,4-Dichlorophenyl)methyl]-5-methyl-1H-1,2,3-triazol-4-yl}carbonyl)amino]-N-methyl-4-pyridinecarboxamide, 1-[(3,4-Dichlorophenyl)methyl]-N-{5-[(ethylamino)carbonyl]-4-methyl-1,3-thiazol-2-yl}-1H-1,2,3-triazole-4-carboxamide, 1-[(3,4-Dichlorophenyl)methyl]-N-{4-methyl-5-[(methylamino)carbonyl]-1,3-thiazol-2-yl}-1H-1,2,3-triazole-4-carboxamide, 1-[(3,4-Dichlorophenyl)methyl]-N-(5-{[(2-hydroxyethyl)amino]carbonyl}-1,3-thiazol-2-yl)-1H-1,2,3-triazole-4-carboxamide, N-[5-(Aminocarbonyl)-1,3-thiazol-2-yl]-1-[(3,4-dichlorophenyl)methyl]-1H-1,2,3-triazole-4-carboxamide, N-[5-(Aminocarbonyl)-4-methyl-1,3-thiazol-2-yl]-1-[(3,4-dichlorophenyl)methyl]-1H-1,2,3-triazole-4-carboxamide, 1-[(3,4-Dichlorophenyl)methyl]-5-methyl-N-1,3,4-thiadiazol-2-yl-1H-1,2,3-triazole-4-carboxamide, 1-[(3,4-Dichlorophenyl)methyl]-N-[5-(hydroxymethyl)-1,3-thiazol-2-yl]-5-methyl-1H-1,2,3-triazole-4-carboxamide, 1-[(3,4-Dichlorophenyl)methyl]-N-[5-(hydroxymethyl)-1,3-thiazol-2-yl]-5-[(methyloxy)methyl]-1H-1,2,3-triazole-4-carboxamide, 1-[(3,4-Dichlorophenyl)methyl]-N-[5-(hydroxymethyl)-4-methyl-1,3-thiazol-2-yl]-5-methyl-1H-1,2,3-triazole-4-carboxamide, 1-[(3,4-Dichlorophenyl)methyl]-N-[5-(hydroxymethyl)-1,3,4-thiadiazol-2-yl]-5-methyl-1H-1,2,3-triazole-4-carboxamide, 1-[(3,4-Dichlorophenyl)methyl]-N-[4-(2-hydroxyethyl)-1,3-thiazol-2-yl]-5-methyl-1H-1,2,3-triazole-4-carboxamide, 1-[(3,4-Dichlorophenyl)methyl]-N-[4-(hydroxymethyl)-2-pyridinyl]-5-methyl-1H-1,2,3-triazole-4-carboxamide, N-{1-[(3,4-Dichlorophenyl)methyl]-5-methyl-1H-1,2,3-triazol-4-yl}-6-(methyloxy)-1,3-benzothiazole-2-carboxamide, or {2-[({1-[(3,4-Dichlorophenyl)methyl]-1H-1,2,3-triazol-4-yl}methyl)amino]-1,3-thiazol-5-yl}methanol.

The compounds of the invention have been found to inhibit SCD activity and may therefore be useful in regulating lipid levels, e.g. plasma lipid levels. Diseases or conditions caused by or associated with an abnormal plasma lipid profile and for the treatment of which the compounds of the invention may be useful include; dyslipidemia, hypoalphalipoproteinemia, hyperbetalipoproteinemia, hypercholesterolemia, hypertriglyceridemia, familial hypercholesterolemia, angina, ischemia, cardiac ischemia, stroke, myocardial infarction, atherosclerosis, obesity, Type I diabetes, Type II diabetes, insulin resistance, hyperinsulinaemia and metabolic syndrome. Other cardiovascular diseases for which the compounds of the present invention are useful include peripheral vascular disease, reperfusion injury, angioplastic restenosis, hypertension, vascular complications of diabetes and thrombosis. Other diseases or conditions include hepatic steatosis, non-alcoholic steatohepatitis (NASH) and other diseases related to accumulation of lipids in the liver.

The compounds of the invention may also be useful in the treatment of skin disorders e.g. eczema, acne, psoriasis, skin ageing, keloid scar formation or prevention, and diseases related to production or secretions from mucous membranes.

The compounds of the invention may also be useful in the treatment of cancer, neoplasia, malignancy, metastases, tumours (benign or malignant), carcinogenesis, hepatomas and the like.

The compounds of the invention may also be useful in the treatment of mild cognitive impairment (MCI), Alzheimer's disease (AD), cerebral amyloid angiopathy (CAA) or dementia associated with Down Syndrome (DS) and other neurodegenerative diseases characterized by the formation or accumulation of amyloid plaques comprising Aβ42.

Within the context of the present invention, the terms describing the indications used herein are classified in the Merck Manual of Diagnosis and Therapy, $17^{th}$ Edition and/or the International Classification of Diseases $10^{th}$ Edition (ICD-10). The various subtypes of the disorders mentioned herein are contemplated as part of the present invention.

In one aspect, the invention provides a compound of formula (I) or a pharmaceutically acceptable salt thereof for use in medical therapy.

In one aspect, the invention provides the use of a compound of formula (I) or a pharmaceutically acceptable salt thereof for the manufacture of a medicament for treating and/or preventing a disease or a condition susceptible to amelioration by an SCD inhibitor.

In another aspect, the invention provides the use of a compound of formula (I) or a pharmaceutically acceptable salt thereof for the manufacture of a medicament for treating and/or preventing acne, psoriasis, skin ageing, cancer, dyslipidemia, hypertriglyceridemia, atherosclerosis, obesity, Type II diabetes, insulin resistance, hyperinsulinaemia, hepatic steatosis and/or non-alcoholic steatohepatitis (NASH).

In another aspect, the invention provides the use of a compound of formula (I) or a pharmaceutically acceptable salt thereof for the manufacture of a medicament for treating and/or preventing acne, psoriasis, skin ageing, cancer, dyslipidemia, atherosclerosis, insulin resistance, hyperinsulinaemia, Type II diabetes and/or hepatic steatosis.

In another aspect, the invention provides the use of a compound of formula (I) or a pharmaceutically acceptable salt thereof for the manufacture of a medicament for treating and/or preventing acne.

In one aspect, the invention provides a compound of formula (I) or a pharmaceutically acceptable salt thereof for use in treating and/or preventing a disease or a condition susceptible to amelioration by an SCD inhibitor in a mammal, including human.

In another aspect, the invention provides a compound of formula (I) or a pharmaceutically acceptable salt thereof for use in treating and/or preventing acne, psoriasis, skin ageing, cancer, dyslipidemia, hypertriglyceridemia, atherosclerosis, obesity, Type II diabetes, insulin resistance, hyperinsulinaemia, hepatic steatosis and/or non-alcoholic steatohepatitis (NASH).

In another aspect, the invention provides a compound of formula (I) or a pharmaceutically acceptable salt thereof for use in treating and/or preventing acne, psoriasis, skin ageing, cancer, dyslipidemia, atherosclerosis, insulin resistance, hyperinsulinaemia, Type II diabetes and/or hepatic steatosis.

In another aspect, the invention provides a compound of formula (I) or a pharmaceutically acceptable salt thereof for use in treating and/or preventing acne.

In one aspect, the invention provides a method for treating and/or preventing a disease or a condition susceptible to amelioration by an SCD inhibitor, which method comprises administering to a subject, for example a mammal, including human, a therapeutically effective amount of a compound of formula (I) or a pharmaceutically acceptable salt thereof.

In another aspect, the invention provides a method for treating and/or preventing a acne, psoriasis, skin ageing, cancer, dyslipidemia, hypertriglyceridemia, atherosclerosis, obesity, Type II diabetes, insulin resistance, hyperinsulinaemia, hepatic steatosis and/or non-alcoholic steatohepatitis (NASH), which method comprises administering to a subject, for example a mammal, including human, a therapeutically effective amount of a compound of formula (I) or a pharmaceutically acceptable salt thereof.

In another aspect, the invention provides a method for treating and/or preventing acne, psoriasis, skin ageing, cancer, dyslipidemia, atherosclerosis, insulin resistance, hyperinsulinaemia, Type II diabetes and/or hepatic steatosis, which method comprises administering to a subject, for example a mammal, including human, a therapeutically effective amount of a compound of formula (I) or a pharmaceutically acceptable salt thereof.

In another aspect, the invention provides a method for treating and/or preventing acne, which method comprises administering to a subject, for example a mammal, including human, a therapeutically effective amount of a compound of formula (I) or a pharmaceutically acceptable salt thereof.

It will be appreciated that reference to "treatment" and "therapy" includes acute treatment or prophylaxis as well as the alleviation of established symptoms.

Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Processes for the preparation of the compounds of formula (I) form further aspects of the invention. $R^1$, $R^2$, $R^3$, $R^4$, $R^5$, $R^6$, $R^7$ and $R^8$ are as defined above unless otherwise specified. Throughout the specification, general formulae are designated by Roman numerals (I), (II), (III), (IV) etc.

In certain instances final compounds of formula (I) can be converted into other compounds of formula (I) by techniques known to those in the art, for example, carboxylic acid substituents can be converted to esters or amides by routine techniques.

In a general process, compounds of formula (I), wherein X represents —CONH— and $R^3$ represents

—Y, wherein

represents —$C_{5-9}$heteroaryl and Y represents —$C_{1-3}$alkyl, —$C_{1-6}$alkoxy, —$CO_2R^4$, —C(=O)$NR^5R^6$, —C(=O)$NHC_{1-3}$alkyl$NR^7R^8$, —C(=O)$NHC_{1-3}$alkyl$OC_{1-3}$alkyl, —C(=O)$NHC_{1-3}$alkylOH, —C(=O)$R^9$, —$C_{1-6}$alkylOH, —C=O, —CHO, —$C_{1-3}$alkyl$CO_2C_{1-3}$alkyl, —$C_{1-3}$alkyl$OC_{1-3}$alkyl, —$C_{1-6}$haloalkyl, —$OC_{1-6}$haloalkyl, —$OC_{3-6}$cycloalkyl, —$C_{3-6}$cycloalkyl or halogen (formula (Ia)), may be prepared according to reaction scheme 1 by reacting compounds of formula (II) and compounds of formula (III). The reaction is suitably carried out in the presence of a coupling reagent such as HATU or EDCI and HOBt and a base such as DIPEA or $NEt_3$ in a suitable solvent such as DMF (suitably at room temperature to 40° C.).

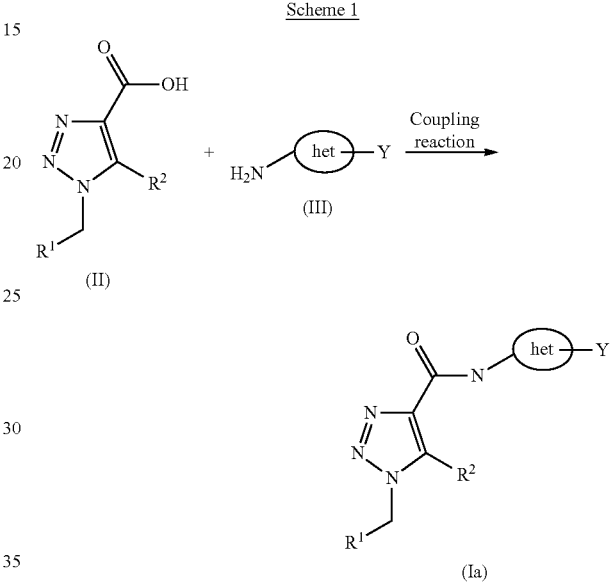

Scheme 1

Accordingly, in one aspect the invention provides a process for the preparation of compounds of the formula (Ia) by reacting compounds of formula (II), wherein $R^1$ and $R^2$ are defined above, with compounds of formula (III) wherein

and Y are defined above, in the presence of a coupling agent.

Compounds of formula (II) may be prepared according to reaction scheme 2 by reacting compounds of formula (IVa) and compounds of formula (IVb). The reaction is suitably carried out in the presence of base such as potassium carbonate in a suitable solvent such as DMF or DMSO (suitably at 40-80° C.) and is followed by saponification of compounds of formula (IV) in basic conditions such as sodium hydroxide in a suitable solvent such as ethanol or methanol (to reflux).

Scheme 2

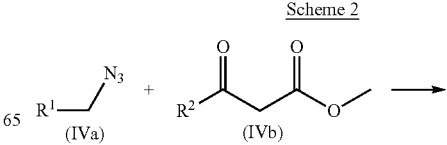

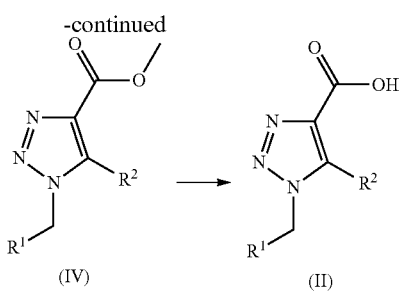

Compounds of formula (II), wherein R² represents H (formula (IIa)), may be prepared according to reaction scheme 3 by reacting compounds of formula (IVa) and ethyl 2-propynoate in a suitable solvent such as ethanol to reflux and is followed by saponification of compounds of formula (V) in basic conditions such as sodium hydroxide in a suitable solvent such as ethanol or methanol (suitably at reflux).

Scheme 3

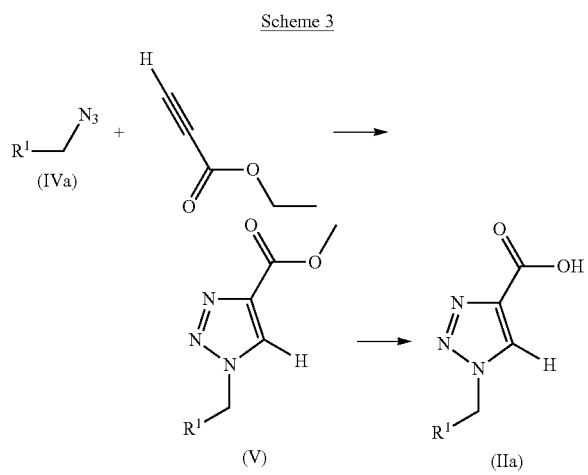

Compounds of formula (IVa) may be prepared according to reaction scheme 4 by the reaction of benzyl halide chlorine or bromine (VI) with sodium azide in a suitable solvent such as DMSO or DMF (suitably at room temperature to 80° C.).

Scheme 4

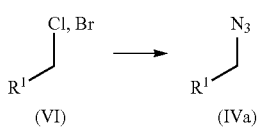

Compounds of formula (I), wherein X represents —NHCO— and R³ represents

wherein

and Y are defined as above (formula (Ib)), may be prepared according to reaction scheme 5 by reacting compounds of formula (VII) and compounds of formula (VIII). The reaction is suitably carried out in the presence of a coupling reagent such as HATU and a base such as DIPEA in a suitable solvent such as DCM or DMF (suitably at room temperature to 40° C.).

Scheme 5

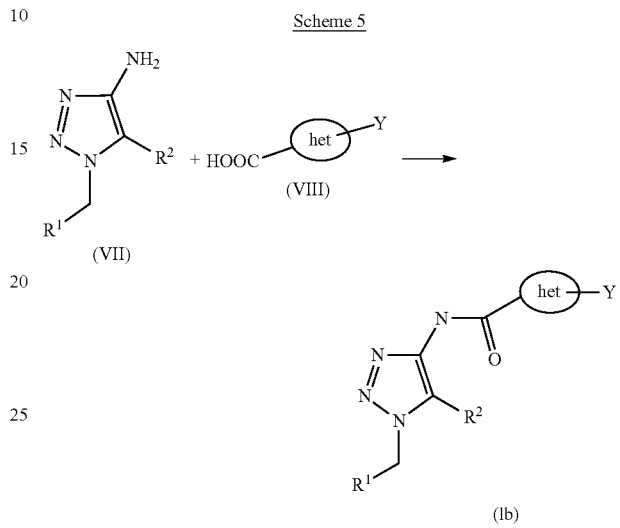

Accordingly, in another aspect the invention provides a process for the preparation of compounds of the formula (Ib) by reacting compounds of formula (VII), wherein R¹ and R² are defined above, with compounds of formula (VIII) wherein

and Y are defined above, in the presence of a coupling reagent.

Compounds of formula (VII), wherein R² represents H, —C₁₋₆alkyl or —C₁₋₃alkylOC₁₋₃alkyl, (formula (VIIa)), may be prepared according to reaction scheme 6 by reacting compounds of formula (VIIb) in the presence of bromine and a base such as potassium hydroxide in a suitable solvent such as water (suitably at 40° to 80° C.).

Scheme 6

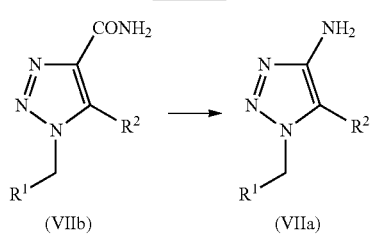

Compounds of formula (VIIb), wherein R² represents H, —C₁₋₆alkyl or —C₁₋₃ alkylOC₁₋₃alkyl may be prepared according to reaction scheme 7 by reacting compounds of formula (II), wherein R² represents —CH₃ (formula (IIb), in the presence of thionyl chloride in chloroform at room temperature, followed by reaction with aqueous ammonia in acetonitrile on ice (e.g. −5 to 5° C.).

Scheme 7

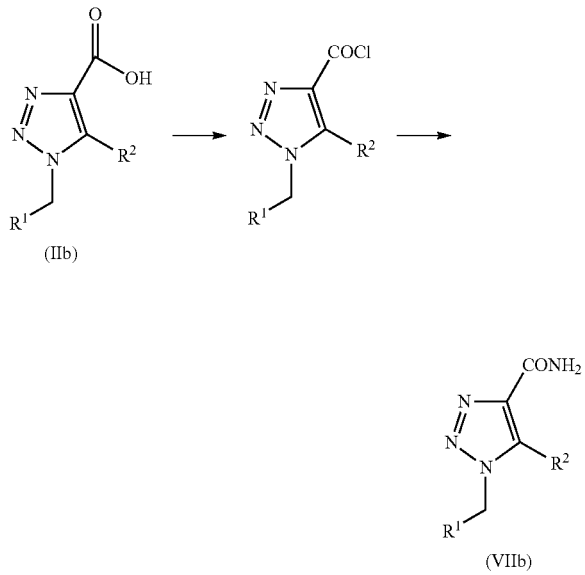

Compounds of formula (I), wherein $R^3$ represents

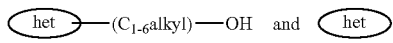

is defined as above (formula (Ic)), may be prepared according to reaction scheme 8 by reduction of the ester function (—COOR$^4$) of compounds of the formula (IX) in the presence of DIBAL-H in a solution of toluene. The reaction is suitably carried out in a solvent such as THF at room temperature.

Scheme 8

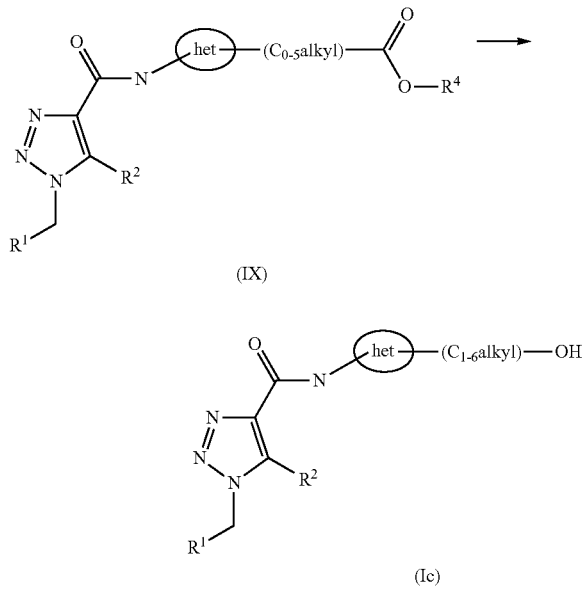

Accordingly, in another aspect the invention provides a process for the preparation of compounds of the formula (Ic) by reduction of the ester function (—COOR$^4$) of compounds of the formula (IX) wherein $R^1$, $R^2$ and het are defined above.

Compounds of formula (I), wherein $R^3$ represents

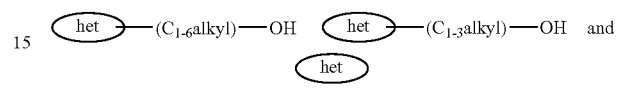

and is defined as above (formula (Ic)), may also be prepared according to reaction scheme 9 by reduction of the aldehyde function (—CHO) of compounds of the formula (X) in the presence of sodium borohydride in a suitable solvent such as DCM/MeOH at room temperature.

Scheme 9

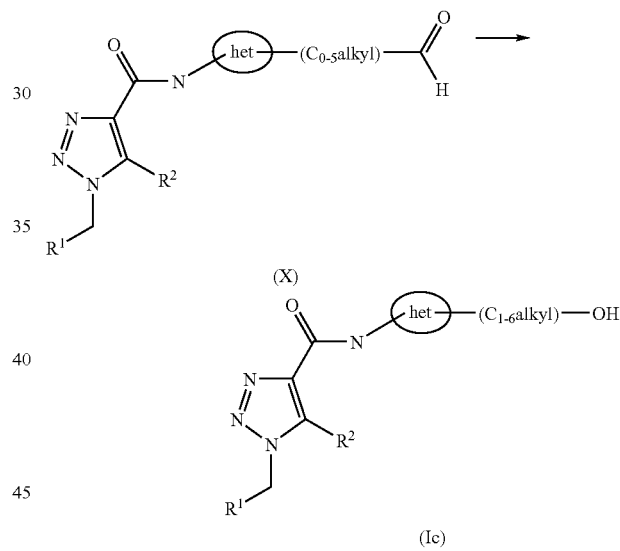

Accordingly, in another aspect the invention provides a process for the preparation of compounds of the formula (Ic) by reduction of the aldehyde function (—CHO) of compounds of the formula (VIIIa) wherein $R^1$, $R^2$ and het are defined above.

Compounds of formula (I), wherein $R^3$ represents

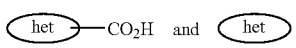

is defined as above (formula (Id)), may be prepared according to reaction scheme 10 by saponification of the ester function (—COOR$^4$) of compounds of the formula (IXa) in basic conditions in a suitable solvent such as methanol or ethanol at reflux.

Scheme 10

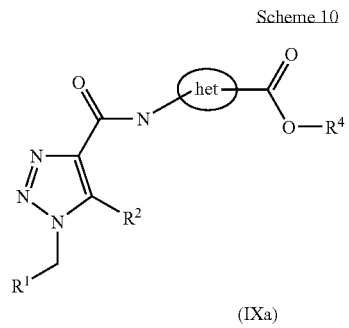

(IXa)

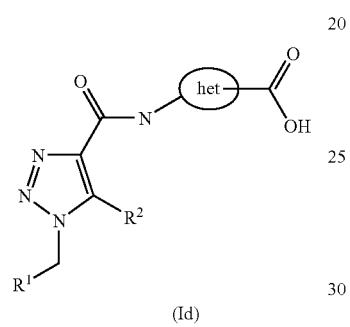

(Id)

Accordingly, in another aspect the invention provides a process for the preparation of compounds of the formula (Id) by saponification of the ester function (—COOR$^4$) of compounds of the formula (IXa) wherein R$^1$, R$^2$ and

are defined above.

Compounds of formula (I), wherein R$^3$ represents

—CONHR and 

is defined as above (formula (Ie)), may be prepared according to reaction scheme 11 by reacting compounds of formula (Id), wherein

is defined as above, and compounds of formula (XI), wherein R represents —R$^5$R$^6$, —C$_{1-3}$alkylNR$^7$R$^8$, —C$_{1-3}$alkylO C$_{1-3}$alkyl or —C$_{1-3}$alkylOH in the presence of a coupling reagent such as HATU and base such as DIPEA in a suitable solvent such as DMF (suitably at room temperature or at 40° C.).

Scheme 11

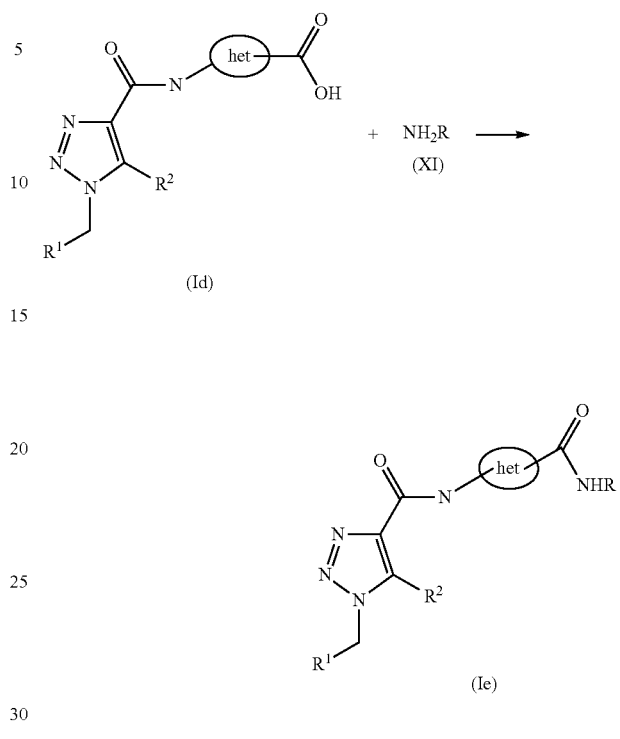

Accordingly, in another aspect the invention provides a process for the preparation of compounds of the formula (Ie) by reacting compounds of the formula (Id), wherein R$^1$, R$^2$ and

are defined above, with compounds of the formula (XI) wherein R is defined above, in the presence of a coupling agent.

Compounds of formula (I), wherein X represents —CH$_2$N— and R$^3$ represents

—Y, wherein

and Y are defined as above, (formula (If)), may be prepared according to reaction scheme 12 by reacting compounds of formula (XII) and compounds of formula (III) in the presence of a base such as potassium carbonate in a suitable solvent such as acetonitrile suitably at 40° C.

Scheme 12

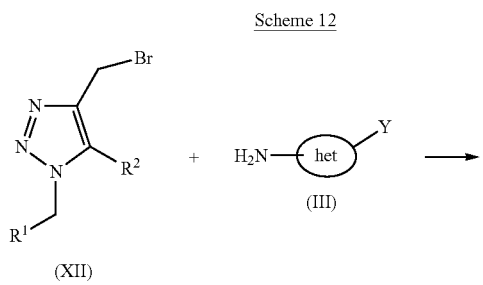

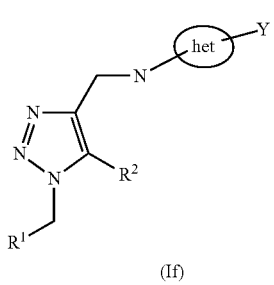

Accordingly, in another aspect the invention provides a process for the preparation of compounds of the formula (If) by reacting compounds of the formula (XIII), wherein $R^1$ and $R^2$ are defined above, with compounds of the formula (III) wherein het and Y are defined above, in the presence of a base.

Compounds of formula (XII) may be prepared according to reaction scheme 13 by the reduction of compounds of formula (IV) using DIBAL in a suitable solvent such as THF to room temperature to give the compound (XIII), followed by the bromination of compounds of the formula (XII) with $PBr_3$ in a suitable solvent such as dichloromethane suitably at room temperature.

Scheme 13

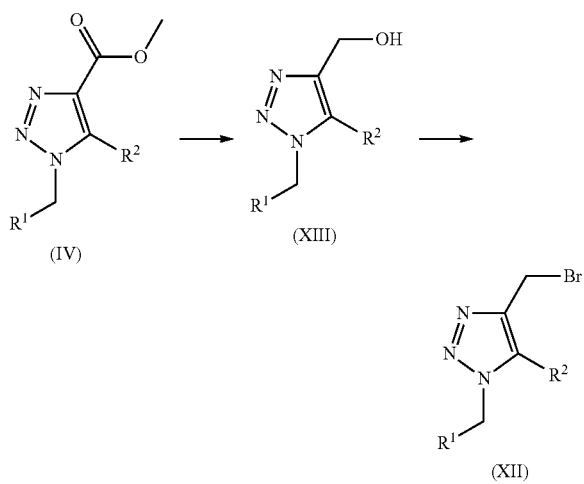

Compounds of the formula (III), (IVb) (VI), (VIII) and (XI) are commercially available compounds or may be prepared by methods known in the literature or processes known to those skilled in the art.

Compounds of the formula (IX), (IXa) and (X) may be prepared according to the general reaction scheme 1.

Further details for the preparation of compounds of formula (I) are found in the examples section hereinafter.

The compounds of the invention may be prepared singly or as compound libraries comprising at least 2, for example 5 to 1,000 compounds, and more preferably 10 to 100 compounds. Libraries of compounds of the invention may be prepared by a combinatorial 'split and mix' approach or by multiple parallel syntheses using either solution phase or solid phase chemistry, by procedures known to those skilled in the art. Thus according to a further aspect there is provided a compound library comprising at least 2 compounds of the invention.

Those skilled in the art will appreciate that in the preparation of compounds of formula (I) and/or salts thereof it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl).

Various intermediate compounds used in the above-mentioned process, including but not limited to certain compounds of formulae (II), (V), constitute a further aspect of the present invention.

The compounds of formula (I) or pharmaceutically acceptable salt(s) thereof may also be used in combination with other therapeutic agents. The invention thus provides, in a further aspect, a combination comprising a compound of formula (I) or pharmaceutically acceptable salt thereof together with one or more further therapeutic agent(s).

Compounds of the invention may be administered in combination with other therapeutic agents. Preferred therapeutic agents are selected from the list: an inhibitor of cholesteryl ester transferase (CETP inhibitors), a HMG-CoA reductase inhibitor, a microsomal triglyceride transfer protein, a peroxisome proliferator-activated receptor activator (PPAR), a bile acid reuptake inhibitor, a cholesterol absorption inhibitor, a cholesterol synthesis inhibitor, a fibrate, niacin, an ion-exchange resin, an antioxidant, an inhibitor of AcylCoA: cholesterol acyltransferase (ACAT inhibitor), a cannabinoid 1 antagonist and a bile acid sequestrant. Other preferred therapeutic agents are selected from the list a corticosteroid, a vitamin D3 derivative, a retinoid, an immunomodulator, an anti androgen, a keratolytic agent, an anti-microbial, a platinum chemotherapeutic, an antimetabolite, hydroxyurea, a taxane, a mitotic disrupter, an anthracycline, dactinomycin, an alkylating agent and a cholinesterase inhibitor.

When the compound of formula (I) or pharmaceutically acceptable salt thereof is used in combination with a second therapeutic agent the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with at least one pharmaceutically acceptable carrier and/or excipient comprise a further aspect of the invention. The individual components of such combinations may be administered either sequentially or simultaneously in separate or combined pharmaceutical formulations by any convenient route.

When administration is sequential, either the SCD inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The invention also includes a pharmaceutical composition comprising one or more compounds of formula (I) or pharmaceutically acceptable salt (s) in combination with one or more excipients.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, dispersions, lotions, creams, gels, pastes, powders, aerosol sprays, syrups or ointments on sponges or cotton applicators, and solutions or suspensions in an aqueous liquid, non-aqueous liquid, oil-in-water emulsion, or water-in-oil liquid emulsion.

Creams, lotions, or ointments, may be prepared as rinse-off or leave-on products, as well as two stage treatment products for use with other skin cleansing or managing compositions. The compositions can be administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention.

Ointments are hydrocarbon-based semisolid formulations containing dissolved or suspended drugs. Creams and lotions are semi-solid emulsion systems and the term is applied both to water/oil or oil/water. Gel formulations are semi-solid systems in which a liquid phase is trapped in a polymeric matrix.

By way of non-limiting example, the ointments may contain one or more hydrophobic carriers selected from, for example, white soft paraffin or other mineral waxes, liquid paraffin, non-mineral waxes, long chain alcohols, long chain acids and silicones. The ointment may contain in addition to the hydrophobic carriers some hydrophillic carriers selected from, for example, propylene glycol and polyethylene glycol in combination with an appropriate surfactant/co-surfactant system. The carrier compositions of the creams or lotions are typically based on water, white soft paraffin and an appropriate surfactant/co-surfactant system, in combination with other carriers/components selected from, for example, propylene glycol, butylene glycol glycerinemonostearate, PEG-glycerinemonostearate, esters such as $C_{12-15}$ alkyl benzoate, liquid paraffin, non-mineral waxes, long chain alcohols, long chain acids silicones, non-silicone polymers. The gels may by way of example be formulated using isopropyl alcohol or ethyl alcohol, propylene glycol and water with a gelling agent such as hydroxyethyl cellulose, suitably in combination with minor components, for example one or more of butylene glycol and a wetting agent such as a poloxamer.

An ointment, cream, lotion, gel, and the like, can further comprise a moisturizing agent. The moisturizing agent can be a hydrophobic moisturizing agent such as ceramide, borage oil, tocopherol, tocopherol linoleate, dimethicone or a mixture thereof or a hydrophilic moisturizing agent such as glycerine, hyaluronic acid, sodium peroxylinecarbolic acid, wheat protein, hair keratin amino acids, or a mixture thereof.

The compositions according to the invention may also comprise conventional additives and adjuvants for dermatological applications, such as preservatives, acids or bases used as pH buffer excipients and antioxidants.

The present invention encompasses administration via a transdermal patch or other forms of transdermal administration. Suitable formulations for transdermal administration are known in the art, and may be employed in the methods of the present invention. For example, suitable transdermal patch formulations for the administration of a pharmaceutical compound are described in, for example, U.S. Pat. No. 4,460,372 to Campbell et al., U.S. Pat. No. 4,573,996 to Kwiatek et al., U.S. Pat. No. 4,624,665 to Nuwayser, U.S. Pat. No. 4,722,941 to Eckert et al., and U.S. Pat. No. 5,223,261 to Nelson et al.

One suitable type of transdermal patch for use in the methods of the present invention encompasses a suitable transdermal patch includes a backing layer which is non-permeable, a permeable surface layer, an adhesive layer substantially continuously coating the permeable surface layer, and a reservoir located or sandwiched between the backing layer and the permeable surface layer such that the backing layer extends around the sides of the reservoir and is joined to the permeable surface layer at the edges of the permeable surface layer. The reservoir contains a compound of formula (I) or pharmaceutically acceptable salt thereof, alone or in combination, and is in fluid contact with the permeable surface layer. The transdermal patch is adhered to the skin by the adhesive layer on the permeable surface layer, such that the permeable surface layer is in substantially continuous contact with the skin when the transdermal patch is adhered to the skin. While the transdermal patch is adhered to the skin of the subject, the compound of formula (I) or pharmaceutically acceptable salt thereof contained in the reservoir of the transdermal patch is transferred via the permeable surface layer, from the reservoir, through the adhesive layer, and to the skin of the patient. The transdermal patch may optionally also include one or more penetration-enhancing agents in the reservoir that enhance the penetration of the compound of formula (I) or pharmaceutically acceptable salt thereof through the skin.

Examples of suitable materials which may comprise the backing layer are well known in the art of transdermal patch delivery, and any conventional backing layer material may be employed in the transdermal patch of the instant invention.

Suitable penetration-enhancing agents are well known in the art as well. Examples of conventional penetration-enhancing agents include alkanols such as ethanol, hexanol, cyclohexanol, and the like, hydrocarbons such as hexane, cyclohexaue, isopropylbenzene; aldehydes and ketones such as cyclohexanone, acetamide, N,N-di(lower alkyl)acetamides such as N,N-diethylacetamide, N,N-dimethyl acetamide, N-(2-hydroxyethyl)acetamide, esters such as N,N-di-lower alkyl sulfoxides; essential oils such as propylene glycol, glycerine, glycerol monolaurate, isopropyl myristate, and ethyl oleate, salicylates, and mixtures of any of the above.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Preparations for oral administration may be suitably formulated to give controlled/extended release of the active compound.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active ingredient, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

The invention also extends to novel intermediates disclosed herein, used in the preparation of compounds of formula (I) or salts thereof.

The following is a list of the used definitions:

DEFINITIONS

APTS Para toluene sulfonic acid
DCM Dichloromethane
DIBAL Diisobutylaluminium hydride solution
DIPEA Diisopropyl ethyl amine
DME 1,2-Dimethoxy ethane
DMF Dimethylformamide
DMSO Dimethyl sulfoxide
EDCI 1,3-Propanediamine $N_3$-(ethylcarbonimidoyl)-$N_1$,$N_1$-dimethyl-, hydrochloride
EtOH Ethanol
HATU O-(7-Azabenzotriazol-1-yl)-1,1,3,3-tetramethyluronium hexafluorophosphate
HCl Hydrochloric acid
HOBt Hydroxy benzotriazole
NaOH Sodium hydroxide
$NEt_3$ Triethylamine
$NH_4Cl$ Ammonium chloride
$PBr_3$ Phosphorus tribromine
Pd tetrakis Tetrakis(triphenylphosphine)palladium (0)
Pd/C Palladium (0) on carbon
THF Tetrahydrofuran Regardless of how the preparation of compounds are represented in the present specification no inference can be drawn that particular batches (or mixtures of two or more batches) of intermediates were used in the next stage of the preparation. The examples and intermediates are intended to illustrate the synthetic routes suitable for preparation of the same, to assist the skilled persons understanding of the present invention.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Analytical Methods LC-MS

Analytical HPLC was conducted on a X-terra MS C18 column (2.5 μm 3*30 mm id) eluting with 0.01M ammonium acetate in water (solvent A) and 100% acetonitrile using the following elution gradient: 0 to 4 minutes, 5 to 100% B; 4 to 5 minutes, 100% B at a flowrate of 1.1 mL/min with a temperature of 40° C.

The mass spectra (MS) were recorded on a micromass ZQ-LC mass spectrometer using electrospray positive ionisation [ES+ve to give MH$^+$ molecular ion] or electrospray negative ionisation [ES−ve to give (M−H)$^-$ molecular ion] modes.

Analytical Methods LC-HRMS

Analytical HPLC was conducted on an Uptisphere-hsc column (3 μm 30*3 mm id) eluting with 0.01M ammonium acetate in water (solvent A) and 100% acetonitrile (solvent B) using the following elution gradient: 0 to 0.5 minutes, 5% B; 0.5 to 3.5 minutes, 5 to 100% B; 3.5 to 4 minutes, 100% B; 4 to 4.5 minutes, 100 to 5% B; 4.5 to 5.5 minutes, 5% B at a flowrate of 1.3 mL/min with a temperature of 40° C.

The mass spectra (MS) were recorded on a micromass LCT, mass spectrometer using electrospray positive ionisation [ES+ve to give MH$^+$ molecular ion] or electrospray negative ionisation [ES−ve to give (M−H)$^-$ molecular ion] modes.

Analytical Method GC-MS

Analytical GC was conducted on a DB-1 ms column (Agilent Technologies), 0.1 μm 10 m*0.1 mm id) eluting with an Helium flow of 0.5 ml/min and pressure at 3.4 bar and with a gradient temperature: 0 to 0.35 min, 100° C.; 0.35 min to 6 min, 100° C. to 250° C. (ramp of 80° C./min).

The mass spectra (MS) were recorded on a Agilent Technologies G5973 mass spectrometer using electronic impact ionisation.

SUPPORTING EXAMPLES AND INTERMEDIATES

The invention is illustrated by the non-limiting Examples described below.

Intermediate 1

(3,4-Dichlorophenyl)methyl azide

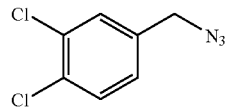

A mixture of 3,4-dichlorobenzyl chloride (10 g, 0.05 mol), sodium azide (5 g, 0.08 mol) in DMSO (100 mL) was stirred at room temperature overnight. The mixture was poured into water (150 mL). The water layer was extracted with EtOAc (100 mL×3). The combined organic phases were dried over sodium sulfate, filtered and concentrated in vacuo. The residue was purified by distillation to give the title compound as an oil (14 g, quantitative yield). LC/MS: m/z 203 (M+H)$^+$. Rt: 2.26 min.

Intermediate 2

Methyl 1-[(3,4-dichlorophenyl)methyl]-5-methyl-1H-1,2,3-triazole-4-carboxylate

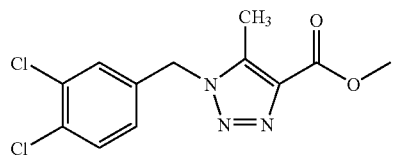

To a suspension of milled potassium carbonate (38.7 g, 0.28 mol) in DMSO (100 mL) was added Intermediate 1 (14 g, 0.07 mol) and methyl acetoacetate (12.1 g, 0.1 mol). The mixture was stirred at 40° C. for 2 days. The mixture was poured into a mixture of ice and water (100 mL). The water was extracted with ethyl acetate (100 mL×2). The combined organic phases were dried over sodium sulfate, filtered and concentrated. The residue was purified by distillation to give the title compound as white solid crystals (14 g, 67%). LC/MS: m/z 301 (M+H)$^+$. Rt: 1.97 min.

The following compounds were similarly prepared by a method analogous to that described for Intermediate 2:

TABLE 1

| Compound | Structure | From | Physical data |
|---|---|---|---|
| Intermediate 3 Methyl 1-[(3,4-dichlorophenyl)methyl]-5-[(methyloxy)methyl]-1H-1,2,3-triazole-4-carboxylate | 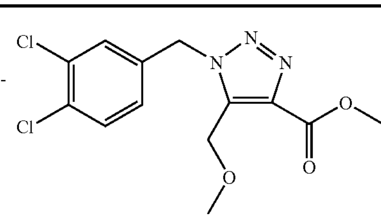 | (3,4-Dichlorophenyl)methyl azide (Intermediate 1) and Ethyl 4-(methyloxy)-3-oxobutanoate | LC/MS: m/z 330 (M + H)$^+$, Rt: 3.12 min |

Intermediate 4

1-[(3,4-Dichlorophenyl)methyl]-5-methyl-1H-1,2,3-triazole-4-carboxylic acid

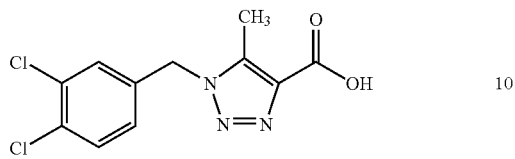

To a mixture of methyl 1-[(3,4-dichlorophenyl)methyl]-5-methyl-1H-1,2,3-triazole-4-carboxylate (Intermediate 2) (9 g, 0.03 mol) in methanol (200 mL) was added NaOH (2.4 g) and water. The mixture was stirred overnight. Water was added and the solvent was evaporated. The residue was extracted with DCM (twice). The aqueous phase was adjusted to pH=2 with a 2N HCl solution. The formed precipitate was filtered to give the title compound as white solid (7.2 g, 84%). LC/MS: m/z 287 (M+H)$^+$. Rt: 2.52 min.

The following compounds were similarly prepared by a method analogous to that described for Intermediate 4:

TABLE 2

| Compound | Structure | From | Physical data |
|---|---|---|---|
| Intermediate 5<br>1-[(3,4-Dichlorophenyl)methyl]-5-[(methyloxy)methyl]-1H-1,2,3-triazole-4-carboxylic acid | ![structure] | Methyl 1-[(3,4-dichlorophenyl)methyl]-5-[(methyloxy)methyl]-1H-1,2,3-triazole-4-carboxylate (Intermediate 3) | LC/MS: m/z 316 (M + H)$^+$, Rt: 2.22 min |

Intermediate 6

2-[({1-[(3,4-Dichlorophenyl)methyl]-5-methyl-1H-1,2,3-triazol-4-yl}carbonyl)amino]-1,3-thiazole-5-carboxylic acid

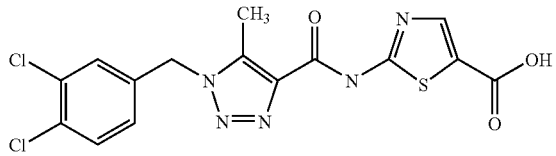

A mixture of methyl 2-[({1-[(3,4-dichlorophenyl)methyl]-5-methyl-1H-1,2,3-triazol-4-yl}carbonyl)amino]-1,3-thiazole-5-carboxylate (Example 4) (0.403 g, 0.95 mmol) and a 1N NaOH solution (10 mL, 9.5 mmol) in EtOH was stirred at reflux for 2 hours. The solvent was evaporated and the residue was acidified with a 1N HCl solution. The precipitate formed was filtered and dried to give the title compound as a white solid (326 mg, 83%). LC/MS: m/z 412 (M+H)$^+$. Rt: 2.48 min.

The following compounds were similarly prepared by a method analogous to that described for Intermediate 6:

TABLE 3

| Compound | Structure | From | Physical data |
|---|---|---|---|
| Intermediate 7<br>2-[({1-[(3,4-Dichlorophenyl)methyl]-5-methyl-1H-1,2,3-triazol-4-yl}carbonyl)amino]-4-pyridinecarboxylic acid | ![structure] | Methyl 2-[({1-[(3,4-dichlorophenyl)methyl]-5-methyl-1H-1,2,3-triazol-4-yl}carbonyl)amino]-4-pyridinecarboxylate (Example 15) | LC/MS: m/z 406 (M + H)$^+$, Rt: 2.47 min |

Intermediate 8

Ethyl 2-[({1-[(3,4-dichlorophenyl)methyl]-5-methyl-1H-1,2,3-triazol-4-yl}carbonyl)amino]-1,3-oxazole-5-carboxylate

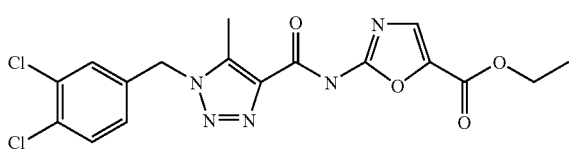

A mixture of 1-[(3,4-dichlorophenyl)methyl]-5-methyl-1H-1,2,3-triazole-4-carboxylic acid (Intermediate 4) (1 g, 3.4 mmol), ethyl 2-amino-1,3-oxazole-5-carboxylate (0.82 g, 5.2 mmol), HOBt (0.708 g, 5.2 mmol), EDCI (1.005 g, 5.2 mmol) and NEt₃ (730 µL, 5.2 mmol) in DMF (50 mL) was stirred at room temperature for 2 days. The reaction was not completed and 2.5 eq of EDCI and HOBt were added and the reaction was heated at 40° C. and stirred for a further 14 days. Again no completed reaction was obtained. The solvent was evaporated and the residue was washed with water and extracted with DCM. The organic phase was dried over sodium sulfate, filtered and concentrated in vacuo. The residue was purified by flash column chromatography eluting with DCM/MeOH (90/10) to give after crystallisation from diisopropyl ether, the title compound as a yellow solid (98 mg, 6%). LC/MS: m/z 424 (M+H)⁺. Rt: 3.17 min.

The following compounds were similarly prepared by a method analogous to that described for Intermediate 8:

DCM and washed with water. The organic phase was dried over sodium sulphate and the solvent was evaporated. The crude azido compound was dissolved in ethanol (100 mL) and ethyl 2-propynoate (1 mL, 1.2 eq) was added. The reaction was stirred to reflux for 24 hours. The reaction was not completed and 0.3 mL of ethyl 2-propynoate was added and the reaction was stirred to reflux for more 24 hours. Ethanol was evaporated and the reaction was dissolved in DCM and washed with water, dried over sodium sulphate and concentrated in vacuo. Purification by flash chromatography eluting with DCM and DCM/MeOH 99/1 gave the title compound as a white solid (1.5 g, 60%). LC/MS: m/z 300 (M+H)⁺. Rt: 3.12 min.

Intermediate 11

1-[(3,4-Dichlorophenyl)methyl]-1H-1,2,3-triazole-4-carboxylic acid

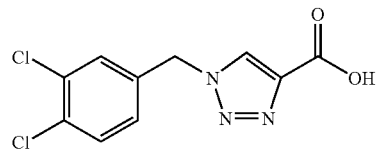

A solution of ethyl 1-[(3,4-dichlorophenyl)methyl]-1H-1,2,3-triazole-4-carboxylate (Intermediate 10) (1.5 g, 5 mmol) and a 1N NaOH solution (7.5 mL, 1.5 eq) in ethanol (50 mL) was stirred at reflux for 48 hours. The solvent was evaporated

TABLE 4

| Compound | Structure | From | Physical data |
|---|---|---|---|
| Intermediate 9<br>1-[(3,4-dichlorophenyl)methyl]-N-(5-formyl-1,3-thiazol-2-yl)-5-[(methyloxy)methyl]-1H-1,2,3-triazole-4-carboxamide | 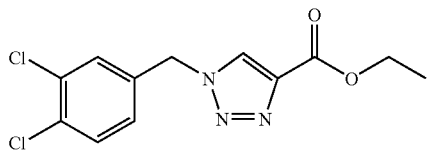 | 1-[(3,4-Dichlorophenyl)methyl]-5-[(methyloxy)methyl]-1H-1,2,3-triazole-4-carboxylic acid (Intermediate 5) and 2-amino-1,3-thiazole-5-carbaldehyde | LC/MS: m/z 426 (M + H)⁺, Rt: 3.15 min |

Intermediate 10

Ethyl 1-[(3,4-dichlorophenyl)methyl]-1H-1,2,3-triazole-4-carboxylate

To a solution of 4-(bromomethyl)-1,2-dichlorobenzene (2 g, 8.3 mmol), in DMF (30 mL) was added sodium azide (0.65 g, 1.2 eq). The reaction was stirred at 80° C. for 3 hours. The solvent was then evaporated and the residue was dissolved in and the residue was acidified with a 1N HCl solution (15 mL). The precipitate formed was filtered, washed with water and dried to give the title compound as a white solid (1.25 g, 92%). LC/MS: m/z 272 (M+H)⁺. Rt: 2.05 min.

Intermediate 12

Methyl 2-[({1-[(3,4-dichlorophenyl)methyl]-1H-1,2,3-triazol-4-yl}carbonyl)amino]-1,3-thiazole-5-carboxylate

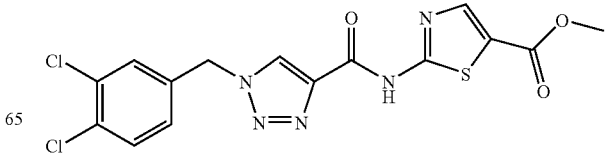

A mixture of 1-[(3,4-dichlorophenyl)methyl]-1H-1,2,3-triazole-4-carboxylic acid (Intermediate 11) (1 g, 3.6 mmol), methyl 2-amino-1,3-thiazole-5-carboxylate (0.58 g, 3.6 mmol), HATU (1.82 g, 1.3 eq) and DIPEA (0.9 mL, 1.3 eq) in DMF (50 mL) was stirred at 40° C. for 3 days. The solvent was evaporated and the residue was washed with water and extracted with DCM. A precipitate was formed, filtered and triturated with a mixture of methanol/acetonitrile. After filtration, the yellow solid was dried to give the title compound as a pale yellow solid (644 mg, 44%). LC/MS: m/z 412 (M+H)$^+$. Rt: 3.21 min.

The following compounds were similarly prepared by a method analogous to that described for Intermediate 12:

TABLE 5

| Compound | Structure | From | Physical data |
|---|---|---|---|
| Intermediate 13 Ethyl 2-[({1-[(3,4-dichlorophenyl)methyl]-1H-1,2,3-triazol-4-yl}carbonyl)amino]-4-methyl-1,3-thiazole-5-carboxylate | 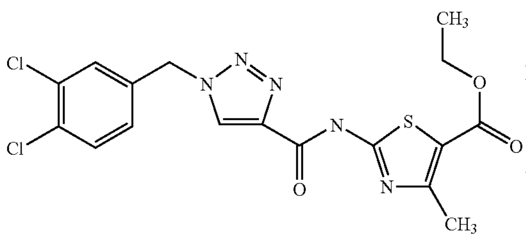 | 1-[(3,4-Dichlorophenyl)methyl]-1H-1,2,3-triazole-4-carboxylic acid (Intermediate 11) and Ethyl 2-amino-4-methylthiazole-5-carboxylate | LC/MS: m/z 438 (M − H)$^+$ Rt: 3.55 min |

Intermediate 14

2-[({1-[(3,4-Dichlorophenyl)methyl]-1H-1,2,3-triazol-4-yl}carbonyl)amino]-1,3-thiazole-5-carboxylic acid

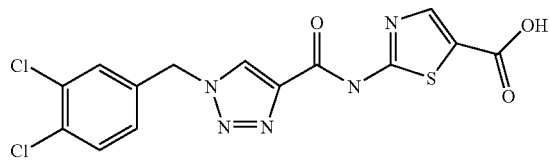

A solution of methyl 2-[{1-[(3,4-dichlorophenyl)methyl]-1H-1,2,3-triazol-4-yl}carbonyl)amino]-1,3-thiazole-5-carboxylate (Intermediate 12) (0.644 g, 1.6 mmol) and a 1N NaOH solution (4.7 mL, 3 eq) in ethanol (40 mL) was stirred at reflux for 3 days. The solvent was evaporated and the residue was acidified with a 1N HCl solution (5 mL). The precipitate formed was filtered, washed with water and dried to give the title compound as a white solid (0.19 g, 30.5%). The filtrate contained a large quantity of the title compound. LC/MS: m/z 398 (M+H)$^+$. Rt: 2.35 min.

The following compounds were similarly prepared by a method analogous to that described for Intermediate 14:

TABLE 6

| Compound | Structure | From | Physical data |
|---|---|---|---|
| Intermediate 15 2-[({1-[(3,4-dichlorophenyl)methyl]-1H-1,2,3-triazol-4-yl}carbonyl)amino]-4-methyl-1,3-thiazole-5-carboxylic acid | 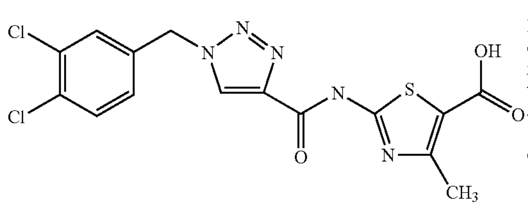 | Ethyl 2-[({1-[(3,4-dichlorophenyl)methyl]-1H-1,2,3-triazol-4-yl}carbonyl)amino]-4-methyl-1,3-thiazole-5-carboxylate (Intermediate 13) | LC/MS: m/z 412 (M + H)$^+$, Rt: 2.41 min |

Intermediate 16

{1-[(3,4-Dichlorophenyl)methyl]-1H-1,2,3-triazol-4-yl}methanol

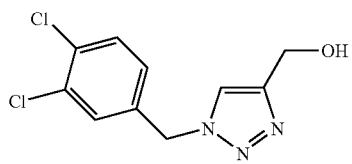

To a solution of ethyl 1-[(3,4-dichlorophenyl)methyl]-1H-1,2,3-triazole-4-carboxylate (Intermediate 10) (0.33 g, 1.09 mmol) in THF was added a 1M solution of DIBAL-H in toluene (2.3 mL, 2.1 eq) and the reaction was stirred at room temperature for 2 hours. The reaction was not completed. Two more equivalents of a 1M solution of DIBAL-H in toluene were added and the reaction was stirred for a further 18 hours. Solid NH$_4$Cl was added followed by water and the aqueous phase was extracted with ether, ethyl acetate, dried over sodium sulphate and evaporated. The title compound was obtained as a white powder after recrystallisation from isopropyl ether (170 mg, 60%). LC/MS: m/z 258 (M+H)$^+$ Rt: 2.45 min.

Intermediate 17

4-(Bromomethyl)-1-[(3,4-dichlorophenyl)methyl]-1H-1,2,3-triazole

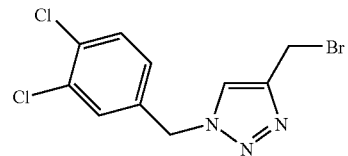

To a solution of {1-[(3,4-dichlorophenyl)methyl]-1H-1,2,3-triazol-4-yl}methanol (Intermediate 16) (0.17 g, 0.66 mmol) in DCM was added PBr$_3$ (125 µL, 2 eq) and the reaction was stirred at room temperature for 3 hours. Water was added, followed by solid NaHCO$_3$. The organic phase was dried over sodium sulphate and evaporated. The title compound was obtained as a colorless oil (0.21 g, 99%) and used in the next step without purification. LC/MS: m/z 320 (M−H)$^+$. Rt: 2.13 min.

Intermediate 18

1-[(3,4-Dichlorophenyl)methyl]-5-methyl-1H-1,2,3-triazole-4-carboxamide

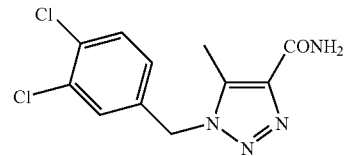

To a solution of (1-[(3,4-dichlorophenyl)methyl]-5-methyl-1H-1,2,3-triazole-4-carboxylic acid) Intermediate 4 (14 g, 48.9 mmol), in chloroform (200 mL) was added thionyl chloride (30 mL) at room temperature. The reaction mixture was stirred to reflux for 4 hours and concentrated in vacuum. The mixture was then dissolved in acetonitrile (50 mL) and aqueous ammonia (50 mL) was added at 0° C. for 30 min. The resulting solid was filtered and dried to give the title compound as white crystals. (12.7 g, 91.1%). LC/MS: m/z 285 (M+H)$^+$. Rt: 2.53 min.

Intermediate 19

1-[(3,4-Dichlorophenyl)methyl]-5-methyl-1H-1,2,3-triazol-4-amine

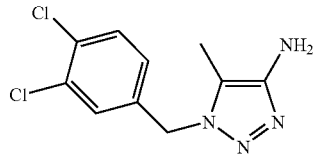

To a solution of potassium hydroxide (10.96 g, 195.8 mmol) in water (50 mL), cooled in an ice-salt bath, was added bromine (6.3 g, 39.16 mmol) and at 0° C., 1-[(3,4-dichlorophenyl)methyl]-5-methyl-1H-1,2,3-triazole-4-carboxamide (Intermediate 18) (9.3 g, 32.63 mmol) was added for 4 hours under vigorous stirring. The reaction mixture was then warmed at 80° C. for 2 days and stirred at room temperature for 12 hours. The resulting solid was filtered and purified by HPLC to give the title compound (3.45 g, 41.14%). LC/MS: m/z 257 (M+H)$^+$. Rt: 2.25 min.

Example 1

1-[(3,4-Dichlorophenyl)methyl]-5-methyl-N-[6-(methyloxy)-1,3-benzothiazol-2-yl]-1H-1,2,3-triazole-4-carboxamide

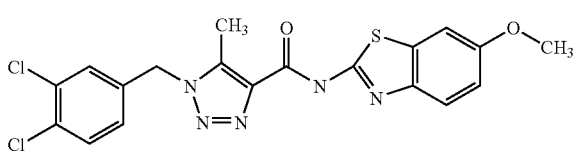

A mixture of 1-[(3,4-dichlorophenyl)methyl]-5-methyl-1H-1,2,3-triazole-4-carboxylic acid (Intermediate 4) (0.1 g, 0.35 mmol), 2-amino-6-methoxybenzothiazole (0.062 g, 0.35 mmol), HATU (0.082 g, 0.45 mmol) and DIPEA (85 µL, 0.45 mmol) in DMF (5 mL) was stirred at 45° C. for 3 days. The solvent was evaporated and the residue was washed with water and extracted with DCM. The organic phase was dried over sodium sulphate, filtered and concentrated in vacuo. The residue was purified by flash chromatography eluting with DCM/MeOH (99/1) to give after trituration in diisopropyl ether, the title compound as a white solid (15 mg, 10%). HRMS calculated for $C_{19}H_{15}Cl_2N_5O_2S$ (M+H)$^+$ 448.0402, found: 448.0403, Rt: 3.31 min. MP: 225° C.

The following compounds were similarly prepared by a method analogous to that described for Example 1:

TABLE 7

| Compound | Structure | From | Physical data |
|---|---|---|---|
| Example 2<br>Ethyl 2-[({1-[(3,4-dichlorophenyl)methyl]-5-methyl-1H-1,2,3-triazol-4-yl}carbonyl)amino]-4-methyl-1,3-thiazole-5-carboxylate | | 1-[(3,4-Dichlorophenyl)methyl]-5-methyl-1H-1,2,3-triazole-4-carboxylic acid (Intermediate 4) and ethyl 2-amino-4-methylthiazole-5-carboxylate | HRMS calculated for $C_{18}H_{17}Cl_2N_5O_3S$<br>Theo: 454.0507<br>Found: 454.0539<br>Rt: 3.34 min |
| Example 3<br>Ethyl 5-[({1-[(3,4-dichlorophenyl)methyl]-5-methyl-1H-1,2,3-triazol-4-yl}carbonyl)amino]-1,3,4-thiadiazole-2-carboxylate | | 1-[(3,4-Dichlorophenyl)methyl]-5-methyl-1H-1,2,3-triazole-4-carboxylic acid (Intermediate 4) and 5-amino-1,3,4-thiadiazole-2-carboxylic acid ethyl ester | HRMS calculated for $C_{16}H_{14}Cl_2N_6O_3S$<br>Theo: 441.0303<br>Found: 441.0278<br>Rt: 2.80 min<br>MP: 203.8° C. |
| Example 4<br>Methyl 2-[({1-[(3,4-dichlorophenyl)methyl]-5-methyl-1H-1,2,3-triazol-4-yl}carbonyl)amino]-1,3-thiazole-5-carboxylate | | 1-[(3,4-Dichlorophenyl)methyl]-5-methyl-1H-1,2,3-triazole-4-carboxylic acid (Intermediate 4) and methyl 2-aminothiazole-5-carboxylate | HRMS calculated for $C_{16}H_{13}Cl_2N_5O_3S$<br>Theo: 426.0194<br>Found: 426.0222<br>Rt: 3.03 min<br>MP: 212° C. |
| Example 5<br>1-[(3,4-Dichlorophenyl)methyl]-N-(5-formyl-1,3-thiazol-2-yl)-5-methyl-1H-1,2,3-triazole-4-carboxamide | | 1-[(3,4-Dichlorophenyl)methyl]-5-methyl-1H-1,2,3-triazole-4-carboxylic acid (Intermediate 4) and 2-amino-1,3-thiazole-5-carbaldehyde | HRMS calculated for $C_{15}H_{11}Cl_2N_5O_2S$<br>Theo: 396.0089<br>Found: 396.0103<br>Rt: 2.86 min<br>MP > 260° C. |
| Example 6<br>1-[(3,4-Dichlorophenyl)methyl]-5-methyl-N-(5-methyl-1,3,4-oxadiazol-2-yl)-1H-1,2,3-triazole-4-carboxamide | | 1-[(3,4-Dichlorophenyl)methyl]-5-methyl-1H-1,2,3-triazole-4-carboxylic acid (Intermediate 4) and 5-methyl-1,3,4-oxadiazol-2-amine | HRMS calculated for $C_{14}H_{12}Cl_2N_6O_2$<br>Theo: 367.0477<br>Found: 367.0500<br>Rt: 2.46 min<br>MP: 192.2° C. |
| Example 7<br>1-[(3,4-Dichlorophenyl)methyl]-5-methyl-N-{5-[(methyloxy)methyl]-1,3,4-thiadiazol-2-yl}-1H-1,2,3-triazole-4-carboxamide | | 1-[(3,4-Dichlorophenyl)methyl]-5-methyl-1H-1,2,3-triazole-4-carboxylic acid (Intermediate 4) and 5-[(methyloxy)methyl]-1,3,4-thiadiazol-2-amine | HRMS calculated for $C_{15}H_{14}Cl_2N_6O_2S$<br>Theo: 413.0354<br>Found: 413.0363<br>Rt: 2.79 min<br>MP: 178.3° C. |
| Example 8<br>Methyl {2-[({1-[(3,4-dichlorophenyl)methyl]-5-methyl-1H-1,2,3-triazol-4-yl}carbonyl)amino]-1,3-thiazol-4-yl}acetate | | 1-[(3,4-Dichlorophenyl)methyl]-5-methyl-1H-1,2,3-triazole-4-carboxylic acid (Intermediate 4) and methyl (2-amino-1,3-thiazol-4-yl)acetate | HRMS calculated for $C_{17}H_{15}Cl_2N_5O_3S$<br>Theo: 440.0351<br>Found: 440.0373<br>Rt: 2.96 min<br>MP: 158° C. |

TABLE 7-continued

| Compound | Structure | From | Physical data |
| --- | --- | --- | --- |
| Example 9 Ethyl 2-[({1-[(3,4-dichlorophenyl)methyl]-5-methyl-1H-1,2,3-triazol-4-yl}carbonyl)amino]-4-(trifluoromethyl)-1,3-thiazole-5-carboxylate | 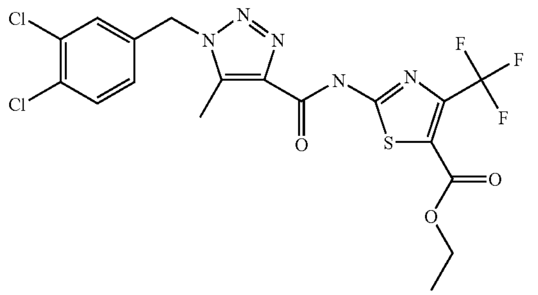 | 1-[(3,4-Dichlorophenyl)methyl]-5-methyl-1H-1,2,3-triazole-4-carboxylic acid (Intermediate 4) and ethyl 2-amino-4-(trifluoromethyl)-1,3-thiazole-5-carboxylate | HRMS calculated for $C_{18}H_{14}Cl_2F_3N_5O_3S$ Theo: 508.0225 Found: 508.0252 Rt: 3.5 min MP: 155° C. |
| Example 10 1-[(3,4-Dichlorophenyl)methyl]-N-(4,5-dimethyl-1,3-thiazol-2-yl)-5-methyl-1H-1,2,3-triazole-4-carboxamide | 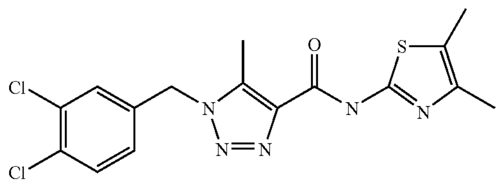 | 1-[(3,4-Dichlorophenyl)methyl]-5-methyl-1H-1,2,3-triazole-4-carboxylic acid (Intermediate 4) and 4,5-dimethyl-1,3-thiazol-2-amine | HRMS calculated for $C_{16}H_{15}Cl_2N_5OS$ Theo: 396.0453 Found: 396.0464 Rt: 3.19 min MP: 210.4° C. |
| Example 11 Ethyl 2-[({1-[(3,4-dichlorophenyl)methyl]-5-methyl-1H-1,2,3-triazol-4-yl}carbonyl)amino]-1,3-benzothiazole-6-carboxylate | 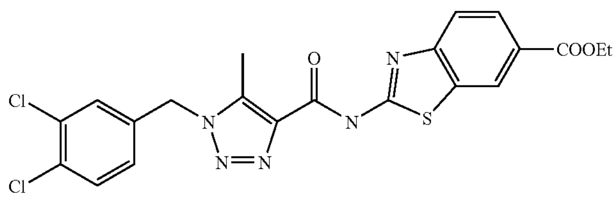 | 1-[(3,4-Dichlorophenyl)methyl]-5-methyl-1H-1,2,3-triazole-4-carboxylic acid (Intermediate 4) and ethyl 2-amino-1,3-benzothiazole-6-carboxylate | HRMS calculated for $C_{21}H_{17}Cl_2N_5O_3S$ Theo: 490.0507 Found: 490.0527 Rt: 3.49 min MP: 199° C. |
| Example 12 Ethyl {2-[({1-[(3,4-dichlorophenyl)methyl]-5-methyl-1H-1,2,3-triazol-4-yl}carbonyl)amino]-5-methyl-1,3-thiazol-4-yl}acetate | 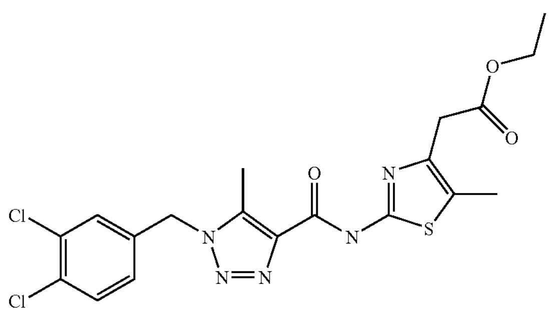 | 1-[(3,4-Dichlorophenyl)methyl]-5-methyl-1H-1,2,3-triazole-4-carboxylic acid (Intermediate 4) and ethyl (2-amino-5-methyl-1,3-thiazol-4-yl)acetate | HRMS calculated for $C_{19}H_{19}Cl_2N_5O_3S$ Theo: 468.0664 Found: 468.0685 Rt: 3.2 min MP: 125° C. |
| Example 13 1-[(3,4-Dichlorophenyl)methyl]-N-(5,7-dioxo-4,5,6,7-tetrahydro[1,3]thiazolo[4,5-d]pyrimidin-2-yl)-5-methyl-1H-1,2,3-triazole-4-carboxamide | 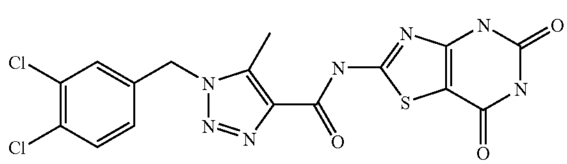 | 1-[(3,4-Dichlorophenyl)methyl]-5-methyl-1H-1,2,3-triazole-4-carboxylic acid (Intermediate 4) and 2-amino[1,3]thiazolo[4,5-d]pyrimidine-5,7(4H,6H)-dione | HRMS calculated for $C_{16}H_{11}Cl_2N_7O_3S$ Theo: 449.9943 Found: 449.9927 Rt: 2.36 min MP: 279.9° C. |
| Example 14 Methyl 6-[({1-[(3,4-dichlorophenyl)methyl]-5-methyl-1H-1,2,3-triazol-4-yl}carbonyl)amino]-3-pyridinecarboxylate | 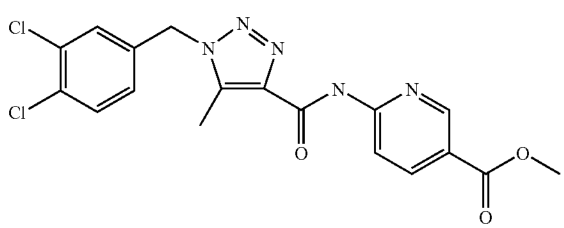 | 1-[(3,4-Dichlorophenyl)methyl]-5-methyl-1H-1,2,3-triazole-4-carboxylic acid (Intermediate 4) and methyl 6-amino-3-pyridinecarboxylate | HRMS calculated for $C_{18}H_{15}Cl_2N_5O_3$ Theo: 420.0630 Found: 420.0626 Rt: 3.2 min MP: 179° C. |

TABLE 7-continued

| Compound | Structure | From | Physical data |
|---|---|---|---|
| Example 15 Methyl 2-[({1-[(3,4-dichlorophenyl)methyl]-5-methyl-1H-1,2,3-triazol-4-yl}carbonyl)amino]-4-pyridinecarboxylate | 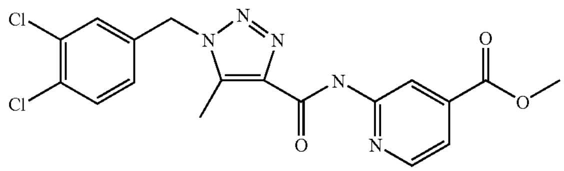 | 1-[(3,4-Dichlorophenyl)methyl]-5-methyl-1H-1,2,3-triazole-4-carboxylic acid (Intermediate 4) and methyl 2-amino-4-pyridinecarboxylate | HRMS calculated for $C_{18}H_{15}Cl_2N_5O_3$ Theo: 420.0630 Found: 420.0633 Rt: 3.18 min MP: 172° C. |

Example 16

2-[({1-[(3,4-Dichlorophenyl)methyl]-5-methyl-1H-1,2,3-triazol-4-yl}carbonyl)amino]-4-methyl-1,3-thiazole-5-carboxylic acid

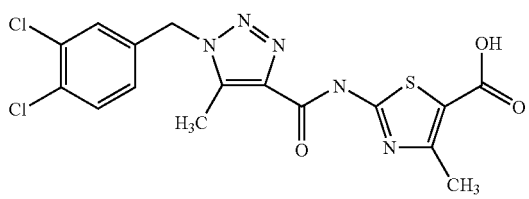

Example 18

1-[(3,4-Dichlorophenyl)methyl]-5-methyl-N-{4-methyl-5-[(methylamino) carbonyl]-1,3-thiazol-2-yl}-1H-1,2,3-triazole-4-carboxamide

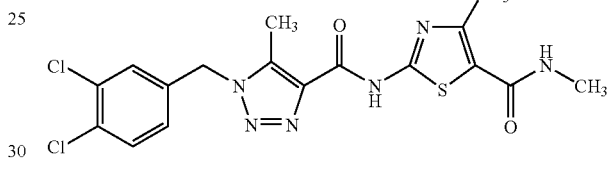

A mixture of ethyl 2-[({1-[(3,4-dichlorophenyl)methyl]-5-methyl-1H-1,2,3-triazol-4-yl}carbonyl)amino]-4-methyl-1,3-thiazole-5-carboxylate (Example 2) (0.482 g, 1.06 mmol) and a 1N NaOH solution (5.5 mL, 5.5 mmol) in ethanol (20 mL) was stirred at 50° C. for 45 min. The reaction was not complete, a 1N NaOH solution (20 mL, 20 mmol) was added and the reaction mixture was stirred for 1 h 30 at 50° C. The solvent was evaporated and the residue was acidified with a 1N HCl solution (25 mL) to pH=1. The precipitate formed was filtered, washed with water and coevaporated with Ethanol. The solid was recrystallised from methanol and washed with DCM to give the title compound as a white solid (418 mg, 92%). HRMS calculated for $C_{16}H_{13}Cl_2N_5O_3S$ (M+H)$^+$ 426.0194, found: 426.0165, Rt: 2.24 min. MP: 262.6° C.

The following compounds were similarly prepared by a method analogous to that described for Example 16:

A mixture of 2-[({1-[(3,4-dichlorophenyl)methyl]-5-methyl-1H-1,2,3-triazol-4-yl}carbonyl)amino]-4-methyl-1,3-thiazole-5-carboxylic acid (Example 16) (0.15 g, 0.35 mmol), methylamine (96 µL, 2.46 mmol), HATU (0.268 g, 0.70 mmol) and DIPEA (80 µL, 0.46 mmol) in DMF was stirred at 40° C. overnight. The solvent was evaporated and the residue was washed with water and extracted with DCM (large volume). The organic phase was dried over sodium sulphate, filtered and concentrated. The residue was twice purified by flash chromatography eluting with DCM/MeOH (95/5) to give after crystallisation from ether the title compound as a white solid (33 mg, 21%). HRMS calculated for $C_{17}H_{16}Cl_2N_6O_2S$ (M+H)$^+$439.0511, found: 439.0548, Rt: 2.69 min. MP: 218.5° C.

The following compounds were similarly prepared by a method analogous to that described for Example 18:

TABLE 8

| Compound | Structure | From | Physical data |
|---|---|---|---|
| Example 17 2-[({1-[(3,4-Dichlorophenyl)methyl]-5-methyl-1H-1,2,3-triazol-4-yl}carbonyl)amino]-1,3-oxazole-5-carboxylic acid | 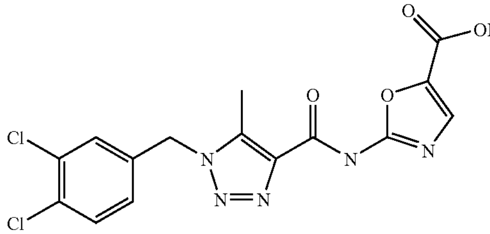 | Ethyl 2-[({1-[(3,4-dichlorophenyl)methyl]-5-methyl-1H-1,2,3-triazol-4-yl}carbonyl)amino]-1,3-oxazole-5-carboxylate (Intermediate 8) | HRMS calculated for $C_{15}H_{11}Cl_2N_5O_4$ Theo: 396.0266 Found: 396.0289 Rt: 2.07 min MP: 201.8° C. |

TABLE 9

| Compound | Structure | From | Physical data |
|---|---|---|---|
| Example 19<br>1-[(3,4-Dichlorophenyl)methyl]-5-methyl-N-(4-methyl-5-{[(3-methylbutyl)amino]carbonyl}-1,3-thiazol-2-yl)-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and isopentylamine | HRMS calculated for $C_{21}H_{24}Cl_2N_6O_2S$<br>Theo: 495.1137<br>Found: 495.1167<br>Rt: 3.22 min.<br>MP: 174.3° C. |
| Example 20<br>1-[(3,4-Dichlorophenyl)methyl]-5-methyl-N-(4-methyl-5-{[(1-methylethyl)amino]carbonyl}-1,3-thiazol-2-yl)-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and isopropylamine | HRMS calculated for $C_{19}H_{20}Cl_2N_6O_2S$<br>Theo: 465.0667<br>Found: 465.0626<br>Rt: 2.94 min.<br>MP: 204.4° C. |
| Example 21<br>1-[(3,4-Dichlorophenyl)methyl]-N-{5-[(ethylamino)carbonyl]-4-methyl-1,3-thiazol-2-yl}-5-methyl-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and ethylamine | HRMS calculated for $C_{18}H_{18}Cl_2N_6O_2S$<br>Theo: 453.0667<br>Found: 453.0684<br>Rt: 2.82 min.<br>MP: 194.1° C. |
| Example 22<br>1-[(3,4-Dichlorophenyl)methyl]-N-[5-({[2-(dimethylamino)ethyl]amino}carbonyl)-4-methyl-1,3-thiazol-2-yl]-5-methyl-1H-1,2,3-triazole-4-carboxamide hydrochloride | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and N,N-dimethylethylenediamine | HRMS calculated for $C_{20}H_{23}Cl_2N_7O_2S$<br>Theo: 496.1089<br>Found: 496.1131<br>Rt: 2.48 min.<br>MP: 121° C. |
| Example 23<br>1-[(3,4-Dichlorophenyl)methyl]-5-methyl-N-(5-{[(3-methylbutyl-amino]carbonyl}-1,3-thiazol-2-yl)-1H-1,2,3-triazole-4-carboxamide | | 2-[({1-[(3,4-Dichlorophenyl)methyl]-5-methyl-1H-1,2,3-triazol-4-yl}carbonyl)amino]-1,3-thiazole-5-carboxylic acid (Intermediate 6) and isopentylamine | HRMS calculated for $C_{20}H_{22}Cl_2N_6O_2S$<br>Theo: 481.0980<br>Found: 481.1023<br>Rt: 3.12 min.<br>MP: 259.3° C. |

TABLE 9-continued

| Compound | Structure | From | Physical data |
|---|---|---|---|
| Example 24<br>1-[(3,4-Dichlorophenyl)methyl]-5-methyl-N-[4-methyl-5-(4-morpholinyl-carbonyl)-1,3-thiazol-2-yl]-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and morpholine | HRMS calculated for $C_{20}H_{20}Cl_2N_6O_3S$<br>Theo: 495.0773<br>Found: 495.0808<br>Rt: 2.71 min.<br>MP: 202.9° C. |
| Example 25<br>1-[(3,4-Dichlorophenyl)methyl]-5-methyl-N-{4-methyl-5-[(4-methyl-1-piperazinyl)carbonyl]-1,3-thiazol-2-yl}-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and 1-methylpiperazine | HRMS calculated for $C_{21}H_{23}Cl_2N_7O_2S$<br>Theo: 508.1089<br>Found: 508.1132<br>Rt: 2.65 min.<br>MP: 216.9° C. |
| Example 26<br>1-[(3,4-Dichlorophenyl)methyl]-5-methyl-N-[4-methyl-5-({[2-(methyloxy)ethyl]amino}carbonyl)-1,3-thiazol-2-yl]-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and 2-methoxyethyl amine | HRMS calculated for $C_{19}H_{20}Cl_2N_6O_3S$<br>Theo: 483.0773<br>Found: 483.0758<br>Rt: 2.75 min.<br>MP: 129° C. |
| Example 27<br>1-[(3,4-Dichlorophenyl)methyl]-N-(5-{[(2-hydroxyethyl)amino]carbonyl}-4-methyl-1,3-thiazol-2-yl)-5-methyl-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and 2-aminoethanol | HRMS calculated for $C_{18}H_{18}Cl_2N_6O_3S$<br>Theo: 469.0616<br>Found: 469.0599<br>Rt: 2.54 min.<br>MP: 166° C. |
| Example 28<br>1-[(3,4-Dichlorophenyl)methyl]-N-{5-[(dimethylamino)carbonyl]-4-methyl-1,3-thiazol-2-yl}-5-methyl-1H-1,2,3-triazole-4-carboxamide | | 2-[({1-[(3,4-Dichlorophenyl)methyl]-5-methyl-1H-1,2,3-triazol-4-yl}carbonyl)amino]-4-methyl-1,3-thiazole-5-carboxylic acid (Example 16) and Dimethyl amine hydrochloride | HRMS calculated for $C_{18}H_{18}Cl_2N_6O_2S$<br>Theo: 453.0667<br>Found: 453.0691<br>Rt: 2.74 min.<br>MP: 144° C. |
| Example 29<br>1-[(3,4-Dichlorophenyl)methyl]-5-methyl-N-{5-[(methylamino)carbonyl]-1,3-thiazol-2-yl}-1H-1,2,3-triazole-4-carboxamide | | 2-[({1-[(3,4-Dichlorophenyl)methyl]-5-methyl-1H-1,2,3-triazol-4-yl}carbonyl)amino]-1,3-thiazole-5-carboxylic acid (Intermediate 6) and methyl amine | HRMS calculated for $C_{16}H_{14}Cl_2N_6O_2S$<br>Theo: 425.0354<br>Found: 425.0347<br>Rt: 2.62 min.<br>MP: 335.6° C. |

TABLE 9-continued

| Compound | Structure | From | Physical data |
|---|---|---|---|
| Example 30<br>1-[(3,4-Dichlorophenyl)methyl]-N-{5-[(dimethylamino)carbonyl]-1,3-thiazol-2-yl}-5-methyl-1H-1,2,3-triazole-4-carboxamide | | 2-[({1-[(3,4-Dichlorophenyl)methyl]-5-methyl-1H-1,2,3-triazol-4-yl}carbonyl)amino]-1,3-thiazole-5-carboxylic acid (Intermediate 6) and dimethyl amine | HRMS calculated for $C_{17}H_{16}Cl_2N_6O_2S$<br>Theo: 439.0511<br>Found: 439.0527<br>Rt: 2.71 min.<br>MP: 304.9° C. |
| Example 31<br>1-[(3,4-Dichlorophenyl)methyl]-N-(5-{[(2-hydroxyethyl)amino]carbonyl}-1,3-thiazol-2-yl)-5-methyl-1H-1,2,3-triazole-4-carboxamide | | 2-[({1-[(3,4-Dichlorophenyl)methyl]-5-methyl-1H-1,2,3-triazol-4-yl}carbonyl)amino]-1,3-thiazole-5-carboxylic acid (Intermediate 6) and 2-aminoethanol | HRMS calculated for $C_{17}H_{16}Cl_2N_6O_3S$<br>Theo: 455.0460<br>Found: 455.0503<br>Rt: 2.51 min.<br>MP: 260.4° C. |
| Example 32<br>2-[({1-[(3,4-Dichlorophenyl)methyl]-5-methyl-1H-1,2,3-triazol-4-yl}carbonyl)amino]-N-methyl-4-pyridinecarboxamide | | 2-[({1-[(3,4-Dichlorophenyl)methyl]-5-methyl-1H-1,2,3-triazol-4-yl}carbonyl)amino]-4-pyridinecarboxylic acid (Intermediate 7) and methyl amine | HRMS calculated for $C_{18}H_{16}Cl_2N_6O_2$<br>Theo: 419.0790<br>Found: 419.0770<br>Rt: 2.70 min.<br>MP: 234.1° C. |

The following compounds were similarly prepared by a method analogous to that described for Example 18:

TABLE 10

| Compound | Structure | From | Physical data |
|---|---|---|---|
| Example 33<br>1-[(3,4-Dichlorophenyl)methyl]-N-{5-[(ethylamino)carbonyl]-4-methyl-1,3-thiazol-2-yl}-1H-1,2,3-triazole-4-carboxamide | | 2-[({1-[(3,4-Dichlorophenyl)methyl]-1H-1,2,3-triazol-4-yl}carbonyl)amino]-4-methyl-1,3-thiazole-5-carboxylic acid (Intermediate 15) and ethyl amine | HRMS calculated for $C_{17}H_{16}Cl_2N_6O_2S$<br>Theo: 439.0511<br>Found: 439.0522<br>Rt: 2.67 min.<br>MP: 210.6° C. |
| Example 34<br>1-[(3,4-Dichlorophenyl)methyl]-N-{4-methyl-5-[(methylamino)carbonyl]-1,3-thiazol-2-yl}-1H-1,2,3-triazole-4-carboxamide | | 2-[({1-[(3,4-Dichlorophenyl)methyl]-1H-1,2,3-triazol-4-yl}carbonyl)amino]-4-methyl-1,3-thiazole-5-carboxylic acid (Intermediate 15) and methyl amine | HRMS calculated for $C_{16}H_{14}Cl_2N_6O_2S$<br>Theo: 425.0354<br>Found: 425.0362<br>Rt: 2.54 min.<br>MP: 210.4° C. |

Example 35

1-[(3,4-Dichlorophenyl)methyl]-N-(5-{[(2-hydroxyethyl)amino]carbonyl}-1,3-thiazol-2-yl)-1H-1,2,3-triazole-4-carboxamide

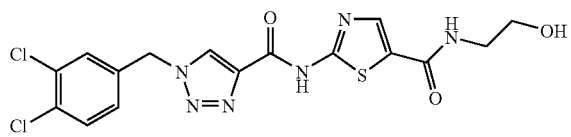

A mixture of 2-[({1-[(3,4-dichlorophenyl)methyl]-1H-1,2,3-triazol-4-yl}carbonyl)amino]-1,3-thiazole-5-carboxylic acid (Intermediate 14) (0.18 g, 0.45 mmol), 2-aminoethanol (32 µL, 1.2 eq), HATU (0.22 g, 1.3 eq) and DIPEA (100 µL, 1.3 eq) in DMF (20 mL) was stirred at 40° C. for 48 hours. The solvent was evaporated and the residue was washed with water and extracted with DCM. The insoluble compound was filtered and washed with a mixture of acetonitrile/methanol 80/20 and then purified by flash chromatography eluting with DCM/MeOH (95/5) to give the title compound as a white solid (60 mg, 30%). HRMS calculated for $C_{16}H_{14}Cl_2N_6O_3S$ (M+H)$^+$441.0303, found: 441.0339, Rt: 2.39 min. MP: 274.8° C.

Example 36

N-[5-(Aminocarbonyl)-1,3-thiazol-2-yl]-1-[(3,4-dichlorophenyl)methyl]-1H-1,2,3-triazole-4-carboxamide

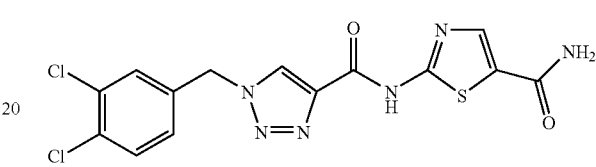

To a suspension of 2-[({1-[(3,4-dichlorophenyl)methyl]-1H-1,2,3-triazol-4-yl}carbonyl)amino]-1,3-thiazole-5-carboxylic acid (Intermediate 14) (0.14 g, 3.5 mmol) in THF (10 mL), was added 1 drop of DMF and oxalyl chloride (0.06 mL, 2 eq). The reaction was stirred to room temperature for 3 hours. The reaction was evaporated in vacuo. After dissolution in THF (10 mL), the residue was treated with ammonia (gas) for 5 min. The reaction was stirred at room temperature for 1 hour. After filtration, the filtrate was concentrated and purified through a bed of silica eluting with DCM/MeOH, 98/2. After recrystallisation from methanol, the title compound was obtained as a white solid (10 mg, 7%). HRMS calculated for $C_{14}H_{10}Cl_2N_6O_2S$ (M+H)$^+$397.0041, found: 397.0044, Rt: 2.40 min. MP: 280.9° C.

The following compounds were similarly prepared by a method analogous to that described for Example 36:

TABLE 11

| Compound | Structure | From | Physical data |
| --- | --- | --- | --- |
| Example 37 N-[5-(Aminocarbonyl)-4-methyl-1,3-thiazol-2-yl]-1-[(3,4-dichlorophenyl)methyl]-1H-1,2,3-triazole-4-carboxamide | 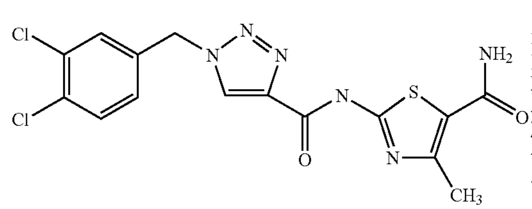 | 2-[({1-[(3,4-Dichlorophenyl)methyl]-1H-1,2,3-triazol-4-yl}carbonyl)amino]-4-methyl-1,3-thiazole-5-carboxylic acid (Intermediate 15) | HRMS calculated for $C_{15}H_{12}Cl_2N_6O_2S$ Theo: 411.0198 Found: 411.0186 Rt: 2.47 min. MP: 283° C. |

Example 38

1-[(3,4-Dichlorophenyl)methyl]-5-methyl-N-1,3,4-thiadiazol-2-yl-1H-1,2,3-triazole-4-carboxamide

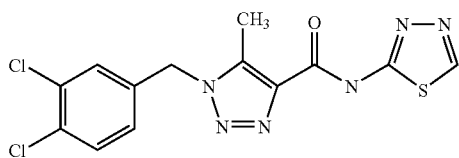

A mixture of ethyl 5-[({1-[(3,4-dichlorophenyl)methyl]-5-methyl-1H-1,2,3-triazol-4-yl}carbonyl)amino]-1,3,4-thiadiazole-2-carboxylate (Example 3) (0.302 g, 0.68 mmol) and a 1N NaOH solution (7 mL, 7 mmol) in ethanol (20 mL) was stirred at 50° C. for 1 hour. The solvent was evaporated and the residue was acidified with a 1N HCl solution. The precipitate formed was filtered and the solid was recrystallised from acetonitrile to give the title compound as a white solid (124 mg, 49%). HRMS calculated for $C_{13}H_{10}Cl_2N_6OS$ (M+H)$^+$369.0092, found: 369.0107, Rt: 2.64 min. MP: 215.6° C.

Example 39

1-[(3,4-Dichlorophenyl)methyl]-N-[5-(hydroxymethyl)-1,3-thiazol-2-yl]-5-methyl-1H-1,2,3-triazole-4-carboxamide

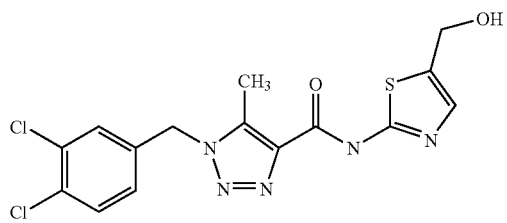

To a suspension of 1-[(3,4-dichlorophenyl)methyl]-N-(5-formyl-1,3-thiazol-2-yl)-5-methyl-1H-1,2,3-triazole-4-carboxamide (Example 5) (1.2 g, 30 mmol), in a mixture of DCM/MeOH, was added sodium borohydride (130 mg). The reaction was stirred at room temperature for 1 hour. After evaporation, the residue was poured in a mixture of water/concentrated HCl solution and extracted with ethyl acetate. A solid was formed and filtered. The filtrate was dried over sodium sulphate and evaporated in vacuo. The combined solids were recrystallised from acetonitrile to give the title compound as a yellow solid (0.8 g, 67%). HRMS calculated for $C_{15}H_{13}Cl_2N_5O_2S$ (M+H)$^+$ 398.0245, found: 398.0205, Rt: 2.59 min. MP: 170.5° C.

The following compounds were similarly prepared by a method analogous to that described for Example 39:

TABLE 12

| Compound | Structure | From | Physical data |
| --- | --- | --- | --- |
| Example 40<br>1-[(3,4-Dichlorophenyl)methyl]-N-5-(hydroxymethyl)-1,3-thiazol-2-yl]-5-[(methyloxy)methyl]-1H-1,2,3-triazole-4-carboxamide | 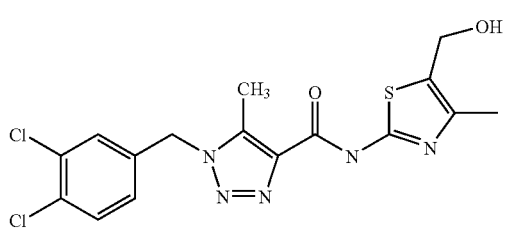 | 1-[(3,4-dichlorophenyl)methyl]-N-(5-formyl-1,3-thiazol-2-yl)-5-[(methyloxy)methyl]-1H-1,2,3-triazole-4-carboxamide (Intermediate 9) | HRMS calculated for $C_{16}H_{15}Cl_2N_5O_3S$<br>Theo: 428.0351<br>Found: 428.0341<br>Rt: 2.65 min.<br>MP: 205° C. |

Example 41

1-[(3,4-Dichlorophenyl)methyl]-N-[5-(hydroxymethyl)-4-methyl-1,3-thiazol-2-yl]-5-methyl-1H-1,2,3-triazole-4-carboxamide To a solution of ethyl 2-[({1-[(3,4-dichlorophenyl)methyl]-5-methyl-1H-1,2,3-triazol-4-yl}carbonyl)amino]-4-methyl-1,3-thiazole-5-carboxylate (Example 2) (0.1 g, 0.22 mmol) in THF was added a 1M solution of DIBAL-H in toluene (2.76 mL, 6 eq) and the reaction was stirred to room temperature for 27 hours. Ether was added followed by solid NH$_4$Cl. After 30 min, water was added and the mixture was filtered. The aqueous phase was extracted with ether, dried over sodium sulphate and evaporated. After purification by flash chromatography, eluting with DCM/MeOH 95/5, and crystallisation from acetonitrile, the title compound was obtained as a white solid (3 mg, 3%). HRMS calculated for $C_{16}H_{15}Cl_2N_5O_2S$ (M+H)$^+$412.0402, found: 412.0409, Rt: 2.65 min. MP: 161.8° C.

The following compounds were similarly prepared by a method analogous to that described for Example 41:

TABLE 13

| Compound | Structure | From | Physical data |
|---|---|---|---|
| Example 42<br>1-[(3,4-Dichlorophenyl)methyl]-N-[5-(hydroxymethyl)-1,3,4-thiadiazol-2-yl]-5-methyl-1H-1,2,3-triazole-4-carboxamide | | Ethyl 5-[({1-[(3,4-dichlorophenyl)methyl]-5-methyl-1H-1,2,3-triazol-4-yl}carbonyl)amino]-1,3,4-thiadiazole-2-carboxylate (Example 3) | HRMS calculated for $C_{14}H_{12}Cl_2N_6O_2S$<br>Theo: 399.0198<br>Found: 399.0216<br>Rt: 2.50 min.<br>MP: 153.6° C. |
| Example 43<br>1-[(3,4-Dichlorophenyl)methyl]-N-[4-(2-hydroxyethyl)-1,3-thiazol-2-yl]-5-methyl-1H-1,2,3-triazole-4-carboxamide | | Methyl {2-[({1-[(3,4-dichlorophenyl)methyl]-5-methyl-1H-1,2,3-triazol-4-yl}carbonyl)amino]-1,3-thiazol-4-yl}acetate (Example 8) | HRMS calculated for $C_{16}H_{15}Cl_2N_5O_2S$<br>Theo: 412.0402<br>Found: 412.0374<br>Rt: 2.69 min.<br>LC/MS: m/z 412 (M + H)$^+$<br>Rt: 3.0 min |
| Example 44<br>1-[(3,4-Dichlorophenyl)methyl]-N-[4-(hydroxymethyl)-2-pyridinyl]-5-methyl-1H-1,2,3-triazole-4-carboxamide | | Methyl 2-[({1-[(3,4-dichlorophenyl)methyl]-5-methyl-1H-1,2,3-triazol-4-yl}carbonyl)amino]-4-pyridine carboxylate (Example 15) | HRMS calculated for $C_{17}H_{15}Cl_2N_5O_2$<br>Theo: 392.0681<br>Found: 392.0716<br>Rt: 2.65 min.<br>MP: 191° C. |

Example 45

N-{1-[(3,4-Dichlorophenyl)methyl]-5-methyl-1H-1,2,3-triazol-4-yl}-6-(methyloxy)-1,3-benzothiazole-2-carboxamide

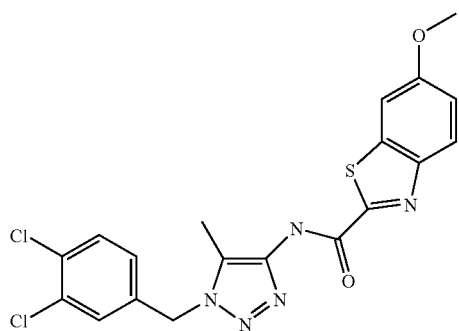

A mixture of 1-[(3,4-dichlorophenyl)methyl]-5-methyl-1H-1,2,3-triazol-4-amine (Intermediate 19) (0.1 g, 0.39 mmol), 6-(methyloxy)-1,3-benzothiazole-2-carboxamide (81 mg, 1 eq), HATU (0.192 g, 1.3 eq) and DIPEA (0.12 mL, 1.3 eq) in DMF (5 mL) was stirred at 45° C. for 48 hours. The solvent was evaporated and the residue was washed with water and extracted with DCM. The organic phase was dried over sodium sulphate, filtered and concentrated. The residue was purified by flash chromatography eluting with DCM/MeOH (99/1) to give after recrystallisation from acetonitrile the title compound as pink pale crystals (110 mg, 65%). HRMS calculated for $C_{19}H_{15}Cl_2N_5O_2S$ (M+H)$^+$ 448.0402, found: 448.0406, Rt: 3.08 min. MP: 176° C.

Example 46

{2-[({1-[(3,4-Dichlorophenyl)methyl]-1H-1,2,3-triazol-4-yl}methyl)amino]-1,3-thiazol-5-yl}methanol

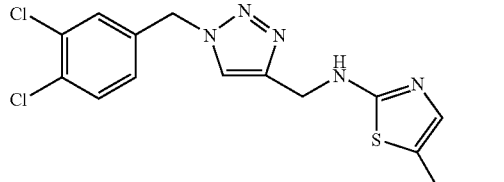

To a solution of 4-(bromomethyl)-1-[(3,4-dichlorophenyl)methyl]-1H-1,2,3-triazole (Intermediate 17) (0.21 g, 0.65 mmol) in acetonitrile was added (2-amino-1,3-thiazol-5-yl)methanol (0.175 g, 2 eq) followed by potassium carbonate (0.185 g, 2 eq)

The reaction was stirred at 40° C. for 2 days. After evaporation, the residue was dissolved in ether and ethyl acetate and washed with water. The organic phase was dried over sodium sulphate, filtered and evaporated. The compound was purified by flash chromatography eluting with DCM/MeOH (92/8). The title compound was obtained as an ochre powder (3 mg, 1.25%). HRMS calculated for $C_{14}H_{13}Cl_2N_5OS$ (M+H)$^+$ 370.0296, found: 370.0297, Rt: 2.35 min. LC/MS: m/z 370 (M+H)+Rt: 2.60 min.

Biological Assay

The compounds of the present invention may be analysed in vitro for SCD activity using an assay based on the production of [$^3$H]H$_2$O, which is released during the enzyme-catalyzed generation of the monounsaturated fatty acyl CoA product. The assay is performed in a 96-well filtration plates. The titrated substrate used in the assay is the [9,10-$^3$H]

stearoyl Coenzyme A. After incubation for 6 minutes of SCD-containing rat microsomes (2 μg protein) and substrate (1 μM), the labelled fatty acid acyl-CoA species and microsomes are absorbed with charcoal and separated from [$^3$H]H$_2$O by centrifugation. The formation of [$^3$H]H$_2$O is used as a measure of SCD activity. Compounds at concentrations starting at 10 μM to 0.1 nM or vehicle (DMSO) are preincubated for 5 minutes with the microsomes before addition of the substrate. The concentration-responses are fitted with sigmoidal curves to obtain IC$_{50}$ values.

All of the synthetic Example compounds 1-46 tested by the above described in vitro assay for SCD activity were found to exhibit an average pIC$_{50}$ value of greater than 5.5.

The following compounds were also prepared and when tested by the above described in vitro assay for SCD activity were found to exhibit an average pIC$_{50}$ value of less than 5.

| Name | Structure |
|---|---|
| 1-[(4-fluorophenyl)methyl]-5-methyl-N-(5-methyl-3-isoxazolyl)-1H-1,2,3-triazole-4-carboxamide | 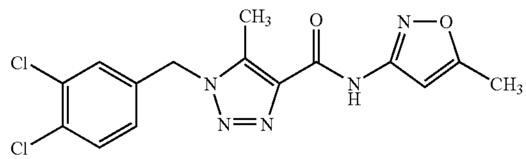 |
| Methyl 2-[({1-[(3,4-dichlorophenyl)methyl]-5-methyl-1H-1,2,3-triazol-4-yl}carbonyl)amino]-1-methyl-1H-imidazole-5-carboxylate | 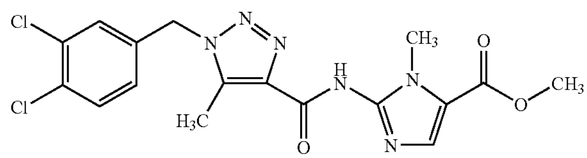 |
| 1-[(3,4-Dichlorophenyl)methyl]-N-(5-formyl-4-methyl-1,3-thiazol-2-yl)-5-methyl-1H-1,2,3-triazole-4-carboxamide | 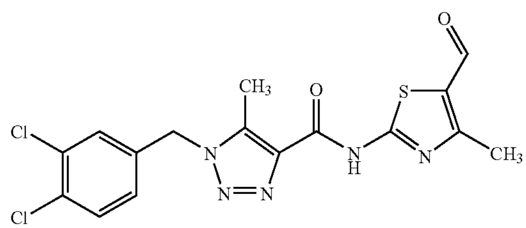 |
| Methyl 2-[({1-[(3,4-dichlorophenyl)methyl]-5-methyl-1H-1,2,3-triazol-4-yl}carbonyl)amino]-5-ethyl-1,3-thiazole-4-carboxylate | 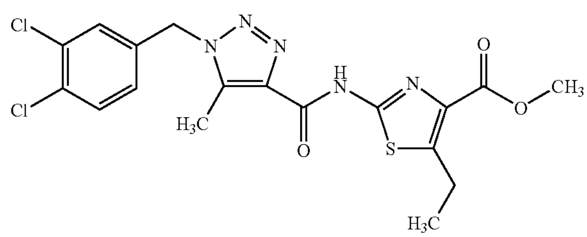 |
| 1-[(3,4-Dichlorophenyl)methyl]-5-methyl-N-[5-(methyloxy)-1,3-benzothiazol-2-yl]-1H-1,2,3-triazole-4-carboxamide | 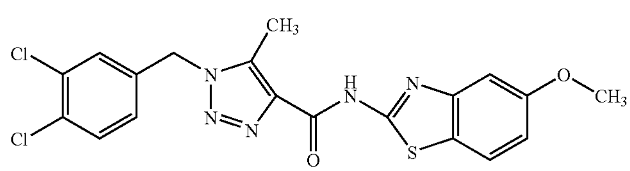 |
| 1-[(3,4-Dichlorophenyl)methyl]-N-[5-(1-hydroxy-1-methylethyl)-1,3,4-thiadiazol-2-yl]-5-methyl-1H-1,2,3-triazole-4-carboxamide | 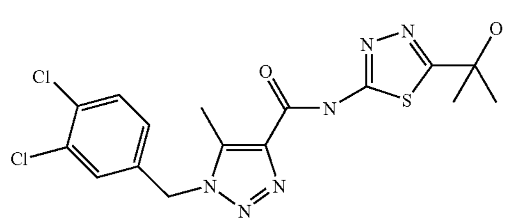 |
| Methyl 6-[({1-[(3,4-Dichlorophenyl)methyl]-5-methyl-1H-1,2,3-triazol-4-yl}carbonyl)amino]-2-pyridinecarboxylate | 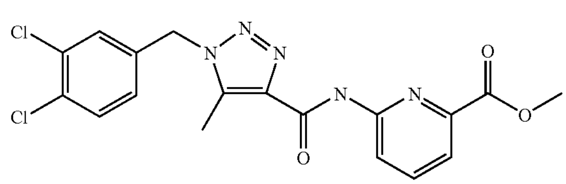 |

The following compounds were also prepared and when tested by the above described in vitro assay for SCD activity were found to exhibit an average $pIC_{50}$ value of between 5 and 5.5.

| Name | Structure |
|---|---|
| 2-[({1-[(3,4-Dichlorophenyl)methyl]-5-methyl-1H-1,2,3-triazol-4-yl}carbonyl)amino]-1-methyl-1H-imidazole-5-carboxylic acid | 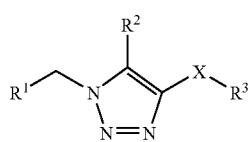 |
| 2-[({1-[(3,4-Dichlorophenyl)methyl]-5-methyl-1H-1,2,3-triazol-4-yl}carbonyl)amino]-1-methyl-1H-imidazole-5-carboxylic acid | |

The invention claimed is:

1. A compound of formula (I):

(I)

wherein:
X represents —CONH—, —NHCO— or —CH$_2$NH—;
R$^1$ represents:
—C$_{6-10}$aryl optionally substituted by one, two or three groups independently selected from:
—C$_{1-3}$alkyl, —C$_{1-6}$alkoxy, —C$_{1-6}$haloalkyl, —OC$_{1-6}$haloalkyl, —OC$_{3-6}$cycloalkyl or halogen;
R$^2$ represents hydrogen, —C$_{1-6}$alkyl or —C$_{1-3}$alkylOC$_{1-3}$alkyl;
R$^3$ represents:
—C$_{5-9}$heteroaryl optionally substituted by one, two or three groups independently selected from: —C$_{1-3}$alkyl, —C$_{1-6}$alkoxy, —CO$_2$R$^4$, —C(=O)NR$^5$R$^6$, —C(=O)NHC$_{1-3}$alkylNR$^7$R$^8$, —C(=O)NHC$_{1-3}$alkylOC$_{1-3}$alkyl, —C(=O)NHC$_{1-3}$alkylOH, —C(=O)R$^9$, —C$_{1-6}$alkylOH, —C(=O), —CHO, —C$_{1-3}$alkylCO$_2$C$_{1-3}$alkyl, —C$_{1-3}$alkylOC$_{1-3}$alkyl, —C$_{1-6}$haloalkyl, —OC$_{1-6}$haloalkyl, —OC$_{3-6}$cycloalkyl, —C$_{3-6}$cycloalkyl or halogen;
R$^4$ represents —H or —C$_{1-3}$alkyl;
R$^5$ represents —H or —C$_{1-3}$alkyl;
R$^6$ represents —H or —C$_{1-6}$alkyl;
R$^7$ represents —H or —C$_{1-3}$alkyl;
R$^8$ represents —H or —C$_{1-3}$alkyl; and
R$^9$ represents —C$_6$heterocycle which is optionally substituted by a group independently selected from: —C$_{1-6}$alkyl;

or a pharmaceutically acceptable salt thereof,
with the proviso that the compound of formula (I) is not N-1,3-benzodioxol-5-yl-1-[(4-fluorophenyl)methyl]-1H-1,2,3-triazole-4-carboxamide

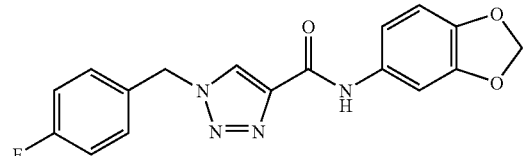

or N-(6-acetyl-1,3-benzodioxol-5-yl)-1-[(4-methylphenyl)methyl]-1H-1,2,3-triazole-4-carboxamide

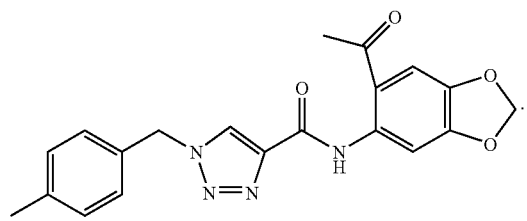

and further provided that R3 is not an optionally substituted tetrahydronapthyridine when X is —NHCO or —CONH.

2. A compound of formula (I) or pharmaceutically acceptable salt thereof according to claim 1 wherein X represents —CONH—.

3. A compound of formula (I) or pharmaceutically acceptable salt thereof according to claim 1 wherein R$^1$ represents phenyl substituted by two groups independently selected from halogen.

4. A compound of formula (I) or pharmaceutically acceptable salt thereof according to claim 1 wherein R$^2$ represents hydrogen or —C$_{1-3}$alkyl.

5. A compound of formula (I) or pharmaceutically acceptable salt thereof according to claim 1 wherein R$^3$ represents —C$_5$heteroaryl containing 5 ring-atoms 1, 2, 3 or 4 of which are hetero-atoms independently selected from nitrogen, oxygen or sulphur and the remaining ring-atoms are carbon, optionally substituted by one, two or three groups independently selected from: —$C_{1-3}$alkyl, —$C_{1-6}$alkoxy, —$CO_2R^4$, —$C(=O)NR^5R^6$, —$C(=O)NHC_{1-3}$alkyl$NR^7R^8$, —$C(=O)$ $NHC_{1-3}$ alkyl$OC_{1-3}$alkyl, —$C(=O)NHC_{1-3}$alkylOH, —$C(=O)R^9$, —$C_{1-6}$alkylOH, —$C(=O)$, —CHO, —$C_{1-3}$ alkyl$CO_2C_{1-3}$alkyl, —$C_{1-3}$alkyl$OC_{1-3}$alkyl, —$C_{1-6}$haloalkyl, —$OC_{1-6}$haloalkyl, —$OC_{3-6}$cycloalkyl, —$C_{3-6}$cycloalkyl or halogen.

6. A compound of formula (I) or pharmaceutically acceptable salt thereof according to claim 1 wherein $R^3$ represents —$C_9$heteroaryl containing 9 ring-atoms 1, 2, 3 or 4 of which are hetero-atoms independently selected from nitrogen or sulphur and the remaining ring-atoms are carbon, optionally substituted by one, two or three groups independently selected from: —$C_{1-3}$alkyl, —$C_{1-6}$alkoxy, —$CO_2R^4$, —$C(=O)NR^5R^6$, —$C(=O)NHC_{1-3}$alkyl$NR^7R^8$, —$C(=O)$ $NHC_{1-3}$alkyl$OC_{1-3}$alkyl, —$C(=O)NHC_{1-3}$alkylOH, —$C(=O)R^9$, —$C_{1-6}$alkylOH, —$C(=O)$, —CHO, —$C_{1-3}$ alkyl$CO_2C_{1-3}$alkyl, —$C_{1-3}$alkyl$OC_{1-3}$alkyl, —$C_{1-6}$haloalkyl, —$OC_{1-6}$haloalkyl, —$OC_{3-6}$cycloalkyl, —$C_{3-6}$cycloalkyl or halogen.

7. A compound of formula (I) or pharmaceutically acceptable salt thereof according to claim 1 wherein $R^3$ represents —$C_6$heteroaryl optionally substituted by one, two or three groups independently selected from: —$C_{1-3}$alkyl, —$C_{1-6}$ alkoxy, —$CO_2R^4$, —$C(=O)NR^5R^6$, —$C(=O)NH$ $C_{1-3}$alkyl$NR^7R^8$, —$C(=O)NHC_{1-3}$alkyl$OC_{1-3}$alkyl, —$C(=O)NHC_{1-3}$alkylOH, —$C(=O)R^9$, —$C_{1-6}$alkylOH, —$C(=O)$, —CHO, —$C_{1-3}$alkyl$CO_2C_{1-3}$alkyl, —$C_{1-3}$ alkyl$OC_{1-3}$alkyl, —$C_{1-6}$haloalkyl, —$OC_{1-6}$haloalkyl, —$OC_{3-6}$ cycloalkyl, —$C_{3-6}$cycloalkyl or halogen.

8. A compound of formula (I) according to claim 1 selected from:
- 1-[(3,4-Dichlorophenyl)methyl]-5-methyl-N-[6-(methyloxy)-1,3-benzothiazol-2-yl]-1H-1,2,3-triazole-4-carboxamide,
- Ethyl 2-[({1-[(3,4-dichlorophenyl)methyl]-5-methyl-1H-1,2,3-triazol-4-yl}carbonyl)amino]-4-methyl-1,3-thiazole-5-carboxylate,
- Ethyl 5-[({1-[(3,4-dichlorophenyl)methyl]-5-methyl-1H-1,2,3-triazol-4-yl}carbonyl)amino]-1,3,4-thiadiazole-2-carboxylate,
- Methyl 2-[({1-[(3,4-dichlorophenyl)methyl]-5-methyl-1H-1,2,3-triazol-4-yl}carbonyl)amino]-1,3-thiazole-5-carboxylate,
- 1-[(3,4-Dichlorophenyl)methyl]-N-(5-formyl-1,3-thiazol-2-yl)-5-methyl-1H-1,2,3-triazole-4-carboxamide,
- 1-[(3,4-Dichlorophenyl)methyl]-5-methyl-N-(5-methyl-1,3,4-oxadiazol-2-yl)-1H-1,2,3-triazole-4-carboxamide,
- 1-[(3,4-Dichlorophenyl)methyl]-5-methyl-N-{5-[(methyloxy)methyl]-1,3,4-thiadiazol-2-yl}-1H-1,2,3-triazole-4-carboxamide,
- Methyl {2-[({1-[(3,4-dichlorophenyl)methyl]-5-methyl-1H-1,2,3-triazol-4-yl}carbonyl)amino]-1,3-thiazol-4-yl}acetate,
- Ethyl 2-[({1-[(3,4-dichlorophenyl)methyl]-5-methyl-1H-1,2,3-triazol-4-yl}carbonyl)amino]-4-(trifluoromethyl)-1,3-thiazole-5-carboxylate,
- 1-[(3,4-Dichlorophenyl)methyl]-N-(4,5-dimethyl-1,3-thiazol-2-yl)-5-methyl-1H-1,2,3-triazole-4-carboxamide,
- Ethyl 2-[({1-[(3,4-dichlorophenyl)methyl]-5-methyl-1H-1,2,3-triazol-4-yl}carbonyl)amino]-1,3-benzothiazole-6-carboxylate,
- Ethyl {2-[({1-[(3,4-dichlorophenyl)methyl]-5-methyl-1H-1,2,3-triazol-4-yl}carbonyl)amino]-5-methyl-1,3-thiazol-4-yl}acetate,
- 1-[(3,4-Dichlorophenyl)methyl]-N-(5,7-dioxo-4,5,6,7-tetrahydro[1,3]thiazolo[4,5-d]pyrimidin-2-yl)-5-methyl-1H-1,2,3-triazole-4-carboxamide,
- Methyl 6-[({1-[(3,4-dichlorophenyl)methyl]-5-methyl-1H-1,2,3-triazol-4-yl}carbonyl)amino]-3-pyridinecarboxylate,
- Methyl 2-[({1-[(3,4-dichlorophenyl)methyl]-5-methyl-1H-1,2,3-triazol-4-yl}carbonyl)amino]-4-pyridinecarboxylate,
- 2-[({1-[(3,4-Dichlorophenyl)methyl]-5-methyl-1H-1,2,3-triazol-4-yl}carbonyl)amino]-4-methyl-1,3-thiazole-5-carboxylic acid,
- 2-[({1-[(3,4-dichlorophenyl)methyl]-5-methyl-1H-1,2,3-triazol-4-yl}carbonyl)amino]-1,3-oxazole-5-carboxylic acid,
- 1-[(3,4-Dichlorophenyl)methyl]-5-methyl-N-{4-methyl-5-[(methylamino)carbonyl]-1,3-thiazol-2-yl}-1H-1,2,3-triazole-4-carboxamide, (example 18)
- 1-[(3,4-Dichlorophenyl)methyl]-5-methyl-N-(4-methyl-5-{[(3-methylbutyl)amino]carbonyl}-1,3-thiazol-2-yl)-1H-1,2,3-triazole-4-carboxamide,
- 1-[(3,4-Dichlorophenyl)methyl]-5-methyl-N-(4-methyl-5-{[(1-methylethyl)amino]carbonyl}-1,3-thiazol-2-yl)-1H-1,2,3-triazole-4-carboxamide,
- 1-[(3,4-Dichlorophenyl)methyl]-N-{5-[(ethylamino)carbonyl]-4-methyl-1,3-thiazol-2-yl}-5-methyl-1H-1,2,3-triazole-4-carboxamide,
- 1-[(3,4-Dichlorophenyl)methyl]-N-[5-({[2-(dimethylamino)ethyl]amino}carbonyl)-4-methyl-1,3-thiazol-2-yl]-5-methyl-1H-1,2,3-triazole-4-carboxamide,
- 1-[(3,4-Dichlorophenyl)methyl]-5-methyl-N-(5-{[(3-methylbutyl)amino]carbonyl}-1,3-thiazol-2-yl)-1H-1,2,3-triazole-4-carboxamide,
- 1-[(3,4-Dichlorophenyl)methyl]-5-methyl-N-[4-methyl-5-(4-morpholinylcarbonyl)-1,3-thiazol-2-yl]-1H-1,2,3-triazole-4-carboxamide,
- 1-[(3,4-Dichlorophenyl)methyl]-5-methyl-N-{4-methyl-5-[(4-methyl-1-piperazinyl)carbonyl]-1,3-thiazol-2-yl}-1H-1,2,3-triazole-4-carboxamide,
- 1-[(3,4-Dichlorophenyl)methyl]-5-methyl-N-[4-methyl-5-({[2-(methyloxy)ethyl]amino}carbonyl)-1,3-thiazol-2-yl]-1H-1,2,3-triazole-4-carboxamide,
- 1-[(3,4-Dichlorophenyl)methyl]-N-(5-{[(2-hydroxyethyl)amino]carbonyl}-4-methyl-1,3-thiazol-2-yl)-5-methyl-1H-1,2,3-triazole-4-carboxamide,
- 1-[(3,4-Dichlorophenyl)methyl]-N-{5-[(dimethylamino)carbonyl]-4-methyl-1,3-thiazol-2-yl}-5-methyl-1H-1,2,3-triazole-4-carboxamide,
- 1-[(3,4-Dichlorophenyl)methyl]-5-methyl-N-{5-[(methylamino)carbonyl]-1,3-thiazol-2-yl}-1H-1,2,3-triazole-4-carboxamide,
- 1-[(3,4-Dichlorophenyl)methyl]-N-{5-[(dimethylamino)carbonyl]-1,3-thiazol-2-yl}-5-methyl-1H-1,2,3-triazole-4-carboxamide,
- 1-[(3,4-Dichlorophenyl)methyl]-N-(5-{[(2-hydroxyethyl)amino]carbonyl}-1,3-thiazol-2-yl)-5-methyl-1H-1,2,3-triazole-4-carboxamide,
- 2-[({1-[(3,4-Dichlorophenyl)methyl]-5-methyl-1H-1,2,3-triazol-4-yl}carbonyl)amino]-N-methyl-4-pyridinecarboxamide,
- 1-[(3,4-Dichlorophenyl)methyl]-N-{5-[(ethylamino)carbonyl]-4-methyl-1,3-thiazol-2-yl}-1H-1,2,3-triazole-4-carboxamide,
- 1-[(3,4-Dichlorophenyl)methyl]-N-{4-methyl-5-[(methylamino)carbonyl]-1,3-thiazol-2-yl}-1H-1,2,3-triazole-4-carboxamide, 1-[(3,4-Dichlorophenyl)methyl]-N-(5-{[(2-hydroxyethyl) amino]carbonyl}-1,3-thiazol-2-yl)-1H-1,2,3-triazole-4-carboxamide, N-[5-(Aminocarbonyl)-1,3-thiazol-2-yl]-1-[(3,4-dichlorophenyl)methyl]-1H-1,2,3-triazole-4-carboxamide, N-[5-(Aminocarbonyl)-4-methyl-1,3-thiazol-2-yl]-1-[(3,4-dichlorophenyl)methyl]-1H-1,2,3-triazole-4-carboxamide, 1-[(3,4-Dichlorophenyl)methyl]-5-methyl-N-1,3,4-thiadiazol-2-yl-1H-1,2,3-triazole-4-carboxamide, 1-[(3,4-Dichlorophenyl)methyl]-N-[5-(hydroxymethyl)-1,3-thiazol-2-yl]-5-methyl-1H-1,2,3-triazole-4-carboxamide, 1-[(3,4-Dichlorophenyl)methyl]-N-[5-(hydroxymethyl)-1,3-thiazol-2-yl]-5-[(methyloxy)methyl]-1H-1,2,3-triazole-4-carboxamide, 1-[(3,4-Dichlorophenyl)methyl]-N-[5-(hydroxymethyl)-4-methyl-1,3-thiazol-2-yl]-5-methyl-1H-1,2,3-triazole-4-carboxamide, 1-[(3,4-Dichlorophenyl)methyl]-N-[5-(hydroxymethyl)-1,3,4-thiadiazol-2-yl]-5-methyl-1H-1,2,3-triazole-4-carboxamide, 1-[(3,4-Dichlorophenyl)methyl]-N-[4-(2-hydroxyethyl)-1,3-thiazol-2-yl]-5-methyl-1H-1,2,3-triazole-4-carboxamide, 1-[(3,4-Dichlorophenyl)methyl]-N-[4-(hydroxymethyl)-2-pyridinyl]-5-methyl-1H-1,2,3-triazole-4-carboxamide, N-{1-[(3,4-Dichlorophenyl)methyl]-5-methyl-1H-1,2,3-triazol-4-yl}-6-(methyloxy)-1,3-benzothiazole-2-carboxamide, or {2-[({1-[(3,4-Dichlorophenyl)methyl]-1H-1,2,3-triazol-4-yl}methyl)amino]-1,3-thiazol-5-yl}methanol, or a pharmaceutically acceptable salt thereof.

9. A pharmaceutical composition comprising a compound of formula (I) or pharmaceutically acceptable salt thereof according to claim 1 and at least one pharmaceutical carrier and/or excipient.

10. A pharmaceutical composition comprising a compound of formula (I) or pharmaceutically acceptable salt thereof according to claim 8 and at least one pharmaceutical carrier and/or excipient.

11. A compound of formula (I) or pharmaceutically acceptable salt thereof according to claim 1 wherein X represents —NHCO—.

12. A compound of formula (I) or pharmaceutically acceptable salt thereof according to claim 1 wherein X represents —CH$_2$NH—.

13. A compound according to claim 1 wherein the C$_{5-9}$heteroaryl is a monocyclic or bicyclic ring system including an aromatic cyclic group containing 5 to 9 ring-atoms 1, 2, 3 or 4 of which are hetero-atoms independently selected from nitrogen, oxygen and sulphur and the remaining ring-atoms are carbon.

14. A compound according to claim 13 wherein the bicyclic structure contains at least one ring which is aromatic.

15. A compound according to claim 1 wherein the C$_{5-9}$heteroaryl is an isoxazole, oxazole, thiazolopyrimidine, imidazole, thiazole, benzothiazole, thiadiazole, oxadiazole or pyridine.

16. A compound according to claim 1 wherein the C$_{5-9}$heteroaryl is a thiazole, benzothiazole, thiadiazole, oxazole, pyridine or thiazolopyrimidine.

* * * * *